United States Patent
Jewett et al.

(10) Patent No.: US 10,954,195 B2
(45) Date of Patent: Mar. 23, 2021

(54) SUBSTITUTED TRIAZENES PROTECTED FROM DEGRADATION BY CARBOXYLATION OF N1

(71) Applicant: ARIZONA BOARD OF REGENTS ON BEHALF OF THE UNIVERSITY OF ARIZONA, Tucson, AZ (US)

(72) Inventors: John C. Jewett, Tucson, AZ (US); Lindsay E. Guzman, Tucson, AZ (US); Bereketab T. Mehari, Tucson, AZ (US); Jie He, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 16/566,659

(22) Filed: Sep. 10, 2019

(65) Prior Publication Data
US 2020/0002290 A1 Jan. 2, 2020

Related U.S. Application Data

(63) Continuation-in-part of application No. PCT/US2018/022046, filed on Mar. 12, 2018, and a continuation-in-part of application No. 15/751,555, filed as application No. PCT/US2016/046624 on Feb. 9, 2018, now Pat. No. 10,472,330.

(60) Provisional application No. 62/469,677, filed on Mar. 10, 2017, provisional application No. 62/203,667, filed on Aug. 11, 2015, provisional application No. 62/203,725, filed on Aug. 11, 2015.

(51) Int. Cl.
C07C 247/16 (2006.01)
C07D 233/88 (2006.01)
C07D 233/60 (2006.01)

(52) U.S. Cl.
CPC ......... *C07D 233/88* (2013.01); *C07D 233/60* (2013.01)

(58) Field of Classification Search
CPC .................................................. C07C 247/16
USPC .......................................................... 552/8
See application file for complete search history.

(56) References Cited

U.S. PATENT DOCUMENTS

| | | | |
|---|---|---|---|
| 3,591,575 A | 7/1971 | Golda | |
| 3,607,542 A | 9/1971 | George et al. | |
| 3,959,210 A | 5/1976 | Lipatova et al. | |
| 4,107,353 A | 8/1978 | Gabriel et al. | |
| 4,218,279 A | 8/1980 | Green | |
| 4,356,050 A | 10/1982 | Crivello et al. | |
| 4,602,073 A | 7/1986 | Skoultchi et al. | |
| 5,856,373 A | 1/1999 | Kaisaki et al. | |
| 8,603,451 B2 | 12/2013 | Zhang et al. | |
| 8,617,827 B2 | 12/2013 | Hell et al. | |
| 8,668,978 B2 | 3/2014 | Malima et al. | |
| 9,085,715 B2 | 7/2015 | Berthelot et al. | |
| 9,458,143 B1 | 10/2016 | Jewett et al. | |
| 9,593,080 B1 | 3/2017 | Jewett et al. | |
| 10,047,061 B2 | 8/2018 | Jewett et al. | |
| 10,125,105 B2 | 11/2018 | Jewett et al. | |
| 2002/0197439 A1 | 12/2002 | Berneth et al. | |
| 2004/0241205 A1 | 12/2004 | Babich et al. | |
| 2005/0080260 A1 | 4/2005 | Mills et al. | |
| 2007/0049587 A1 | 3/2007 | Zbinden et al. | |
| 2007/0098807 A1 | 5/2007 | Babich et al. | |
| 2007/0104719 A1 | 5/2007 | Carter et al. | |
| 2009/0048222 A1 | 2/2009 | Bell et al. | |
| 2009/0286308 A1 | 11/2009 | Berthelot et al. | |
| 2011/0245287 A1 | 10/2011 | Holaday et al. | |
| 2017/0114033 A1 | 4/2017 | Jewett et al. | |

(Continued)

FOREIGN PATENT DOCUMENTS

| | | |
|---|---|---|
| DE | 265008 A1 | 2/1989 |
| DE | 4242428 A1 | 10/1993 |
| WO | WO 2008/090554 A2 | 7/2008 |

(Continued)

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

(Continued)

*Primary Examiner* — Douglas M Willis
(74) *Attorney, Agent, or Firm* — Nguyen Tarbet LLC

(57) ABSTRACT

Triazabutadiene molecules, such as those according to Formula B, which can yield aryl diazonium species, and methods of use of triazabutadiene molecules, for example methods and compositions for yielding an aryl diazonium species from a triazabutadiene molecule, e.g., a protected aryl diazonium species in the form of a triazabutadiene. In some embodiments, an enzyme catalyzes the reaction yielding the aryl diazonium species from the triazabutadiene molecule. As an example, the methods and compositions herein may be used for delivery of drugs.

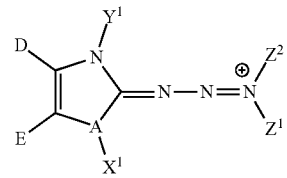

Formula B

8 Claims, 13 Drawing Sheets

(56) References Cited

U.S. PATENT DOCUMENTS

2018/0230106 A1  8/2018  Jewett et al.

FOREIGN PATENT DOCUMENTS

| WO | WO 2009/137916 A1 | 11/2009 |
|---|---|---|
| WO | WO2015073746 A2 | 5/2015 |
| WO | WO2015191735 A1 | 12/2015 |
| WO | WO2017027743 A1 | 2/2017 |
| WO | WO2017180889 A1 | 10/2017 |
| WO | WO2018023130 A1 | 2/2018 |
| WO | WO 2018165666 A1 | 9/2018 |

OTHER PUBLICATIONS

Kimani et al., Water-soluble Triazabutadienes that Release Diazonium Species upon Protonation under Physiologically Relevant Conditions, Angewandte Chemie International Edition, vol. 54, Feb. 6, 2015 [retrieved on Nov. 18, 2016). Retrieved from the Internet: <URL:http://onlinelibrary.wiley.com/doi10.1 002Ianie.201411277/abstract; jsessionid=878CB7308B68B03C6CDEA4579EA97B54.f03t01>. pp. 4051-4054.
Zhong et al., 2014, Nature Nanotechnology 9, 858-866.
Stewart et al., 2011, J Polym Sci B Polym Phys 49(11):757-771.
Poulsen et al., 2014, Biofouling 30(4):513-23.
Stewart, 2011, Appl Microbiol Biotechnol 89(1):27-33.
Stewart et al.,, 2011, Adv Colloid Interface Sci 167(1-2):85-93.
Hennebert et al., 2015, Interface Focus 5(1):2014.
Y. Modis, S. Ogata, D. Clements, S. C. Harrison, Nature 2004, 427, 313-319.
C. D. Blanchette, Y. H. Woo, C. Thomas, N. Shen, T. A. Sulchek, A. L. Hiddessen, PLoS One 2009, 4, e6056.
J. Han, K. Burgess, Chem. Rev. 2010, 110, 2709-2728.
J. Kalia, R. T. Raines, Angew. Chem. Int. Ed. Engl. 2008, 47, 7523-7526.
J. Kalia, R. T. Raines, Angew. Chem. 2008, 120, 7633-7636.
J. Z. Du, X. J. Du, C. Q. Mao, J. Wang, J. Am. Chem. Soc. 2011, 133, 17560-17563.
E. H. Cordes, H. G. Bull, Chem. Rev. 1974, 74, 581-603.
A. Luong, T. Issarapanichkit, S. D. Kong, R. Fonga, J. Yang, Org. Biomol. Chem. 2010, 8, 5105-5109.
Fanghänel, R. Hänsel, W. Ortmann, J. Hohlfeld, J. Prakt. Chem. 1975, 317, 631-640.
H.-T. Dorsch, H. Hoffmann, R. Hansel, G. Rasch, E. Fanghänel, J. Prakt. Chem. 1976, 318, 671-680.
E. Fanghänel, R. Hänsel, J. Hohlfeld, J. Prakt. Chem. 1977, 319, 485-493.
E. Fanghänel, H. Poleschner, R. Radeglia, R. Hänsel, J. Prakt. Chem. 1977, 319, 813-826.
E. Fanghänel, J. Hohlfeld, J. Prakt. Chem. 1981, 323, 253-261.
R. Radeglia, R. Wolff, T. Steiger, S. Simova, E. Fanghanel, J. Prakt. Chem. 1984, 5, 511-514.
E. Fanghänel, W. Ortmann, A. Hennig, J. Prakt. Chem. 1988, 330, 27-34.
E. Fanghänel, W. Ortmann, J. Prakt. Chem. 1989, 331, 721-725.
E. Fanghänel, J. U. Bauroth, H. Hentschel, F. Gußmann, H. Alzyadi, W. Ortmann, J. Prakt.Chem. 1992, 334, 241-247.
D. M. Khramov, C. W. Bielawski, Chem. Commun. 2005, 4958-4960.
S. Dahmen, S. Brase, Org. Lett. 2000, 2, 3563-3565.
S. Brase, Acc. Chem. Res. 2004, 37, 805-816.
D. Jishkariani, C. D. Hall, A. Demircan, B. J. Tomlin, P. J. Steel, A. R. Katritzky, J. Org. Chem. 2013, 78, 3349-3354.
D. M. Khramov, C. W. Bielawski, J. Org. Chem. 2007, 72, 9407-9417.
A. G. Tennyson, E. J. Moorhead, B. L. Madison, J. A. V. Er, V. M. Lynch, C. W. Bielawski, Eur. J. Org. Chem. 2010, 6277-6282.
W. Herrmann, C. Köcher, Angew. Chem. Int. Ed. 1997, 36, 2162-2187.
W. Herrmann, C. Köcher, Angew. Chem. 1997, 109, 2256-2282.
N. Marion, S. Díez-González, S. P. Nolan, Angew. Chem. Int. Ed. Engl. 2007, 46, 2988-3000.
N. Marion, S. Díez-González, S. P. Nolan, Angew. Chem. 2007, 119, 3046-3058.
A. F. Hegarty, in The Chemistry of Diazonium and Diazo Groups, vol. 2 (Ed.: S. Patai), John Wiley & Sons, Ltd., New York, NY, 1978, pp. 511-591.
L. P. Hammett, J. Am. Chem. Soc. 1937, 59, 96-103.
B. M. Tracey, D. E. G. Shuker, Chem. Res. Toxicol. 1997, 10, 1378-1386.
J. M. Hooker, E. W. Kovacs, M. B. Francis, J. Am. Chem. Soc. 2004, 126, 3718-3719.
J. Gavrilyuk, H. Ban, M. Nagano, W. Hakamata, C. F. Barbasiii, Bioconjugate Chem. 2012, 23, 2321-2328.
L. Wang, V. Gruzdys, N. Pang, F. Meng, X.-L. Sun, RSC Adv. 2014, 4, 39446.
European Journal of Inorganic Chemistry vol. 2013, Issue 12, p. 2020-2030, Apr. 2013 Elena García-Moreno, Elena Cerrada, M. José Bolsa, Asunción Luquin and Mariano Laguna.
European Journal of Medicinal Chemistry vol. 46, Issue 7, Jul. 2012, p. 2748-2758, Marijana Hranjeca, Borka Lučića, Ivana Ratkajb, Sandra Kraljević Pavelićb, Ivo Piantanidac, Krešimir Pavelićb, Grace Karminski-Zamola.
Phosphate-buffered saline (PBS) CSH Protocols. "http://cshprotocols.cshlp.org/content/2006/1/pdb.rec8247".
Cornaii, Development of Clickable Triazabutadienes as Cleavable Cross-linkers', A thesis submitted to the Faculty of the Department of Chemistry and Biochemistry in Partial Fulfillment of the Requirements for the Degree of Master of Science, The University of Arizona, Apr. 8, 2016.
International Search Report Issued for PCT Application No. PCT/US15/35136 dated Sep. 14, 2015.
International Search Report Issued for PCT Application No. PCT/US17/44737 dated Dec. 11, 2017.
International Search Report Issued for PCT Application No. PCT/US16/46624 dated Dec. 9, 2016.
Pubchem, SID 42688522, Dec. 5, 2007 [retrieved on Nov. 18, 2016].
International Search Report Issued for PCT Application No. PCT/US18/22046 dated May 22, 2018.
Guzman et al. Protecting Triazabutadienes to Afford Acid Resistance, ChemBioChem Sep. 23, 2016. vol. 17, p. 2220-2222.
Arlett, J. L., Myers, E. B., & Roukes, M. L. (2011). Comparative advantages of mechanical biosensors. Nature Nanotechnology, 6(4), 203-215. http://doi.org/10.1038/nnano.2011.44.
Gooding, J. J., & Darwish, N. (2012). The rise of self-assembled monolayers for fabricating electrochemical biosensors—an interfacial perspective. Chemical Record, 12(1), 92-105. http://doi.org/10.1002/tcr.201100013.
Grieshaber, D., Mackenzie, R., Vörös, J., & Reimhult, E. (2008). Electrochemical Biosensors—Sensor Principles and Architectures. Sensors, 8(3), 1400-1458. http://doi.org/10.3390/s8031400.
Gwent Systems, G. A. M. (n.d.). Electrochemical Biosensor Materials. Retrieved from http://www.gwent.org/presentations/biosensors.pdf.
Jung, J., & Lim, S. (2013). ZnO nanowire-based glucose biosensors with different coupling agents. Applied Surface Science, 265, 24-29. http://doi.org/10.1016/j.apsusc.2012.10.069.
Mahouche-Chergui, S., Gam-Derouich, S., Mangeney, C., & Chehimi, M. M. (2011). Aryl diazonium salts: a new class of coupling agents for bonding polymers, biomacromolecules and nanoparticles to surfaces. Chemical Society Reviews, 40(7), 4143-4166. http://doi.org/10.1039/c0cs00179a.
Reyes De Corcuera, J., & Cavalieri, R. (2003). Biosensors. Encyclopedia of Agricultural, Food, and Biological Engineering, 119-123. http://doi.org/10.1081/E-EAFE.
Smith, R. K., Lewis, P. A., & Weiss, P. S. (2004). Patterning self-assembled monolayers. Progress in Surface Science, 75(1-2), 1-68. http://doi.org/10.1016/j.progsurf.2003.12.001.
Thévenot, D. R., Toth, K., Durst, R. A., & Wilson, G. S. (2001). Electrochemical biosensors: Recommended definitions and classi-

(56) References Cited

OTHER PUBLICATIONS fication. Biosensors and Bioelectronics, 16(1-2), 121-131. http://doi.org/10.1016/S0956-5663(01)00115-4.
Addy et al. 'A Chemoselective Rapid Azo-Coupling Reaction (CRACR) for "Unclickable" Bioconjugation', J Am Chem Soc. 2017, vol.139(34), pp. 11670-11673. doi:10.1021/jacs.7b05125.
Jensen et at 'Light-Activated Triazabutadienes for the Modification of a Viral Surface', Chembiochem. 2016, vol. 17 (23), pp. 1216-2219. doi:10.1002/cbic.20160050B.
International Search Report Issued for PCT Application No. PCT/US19/13996 dated Apr. 29, 2019.

* cited by examiner (i)

(ii) base-blocking steric wall / non-blocking steric wall (iii)

(i)

(ii)

| Compound | Ar = | $\lambda_{max}$ (nm) | $\varepsilon$ (cm⁻¹M⁻¹) |
|---|---|---|---|
| A ● | Ph | 370 | 14300 |
| C ■ | m-NO₂Ph | 361 | 16700 |
| D ▲ | p-CNPh | 395 | 24300 |
| E ◆ | p-NO₂Ph | 441 | 17900 |

(iii)

| R[1] | R[2] | rate (M$^{-1}$s$^{-1}$) |
|---|---|---|
| Me | Et | 7.7 ± 0.8 |
| OMe | Et | ND |
| CF$_3$ | Et | 2.1 ± 0.8 |
| NO$_2$ | Et | 9.1 ± 1.8 |
| H | Et | 13.5 ± 1.5 |
| H | neopent | 13.6 ± 0.9 |
| H | i-Pr | 5.7 ± 0.8 |

Rapid diazonium release at pH 7

SUBSTITUTED TRIAZENES PROTECTED FROM DEGRADATION BY CARBOXYLATION OF N1

CROSS-REFERENCE TO RELATED APPLICATIONS

This application is continuation-in-part of PCT Patent Application No. PCT/US18/22046 filed Mar. 12, 2018, which claims benefit of U.S. Provisional Patent Application No. 62/469,677 filed Mar. 10, 2017, the specifications of which are incorporated herein in their entirety by reference.

This application is a continuation-in-part and claims benefit of U.S. patent application Ser. No. 15/751,555 filed Feb. 9, 2018, which is a 371 application of PCT Patent Application No. PCT/US16/46624 filed Aug. 11, 2016, which claims benefit of U.S. Provisional Patent Application No. 62/203,667 filed Aug. 11, 2015 and U.S. Provisional Patent Application No. 62/203,725 filed Aug. 11, 2015, the specifications of which are incorporated herein in their entirety by reference.

STATEMENT REGARDING FEDERALLY SPONSORED RESEARCH OR DEVELOPMENT

This invention was made with government support under Grant No. 1552568 awarded by NSF. The government has certain rights in the invention.

FIELD OF THE INVENTION

The present invention relates to protected aryl diazonium species that can be selectively released using enzymes.

BACKGROUND OF THE INVENTION

Degradation of triazabutadiene molecules to their respective diazonium species is triggered by a protonation event on the N3 nitrogen atom (farthest from the aryl ring). In an effort to understand the reactivity of triazabutadienes, Fanghanel et al. (J. Prakt. Chem. 1977, 319:813-826) showed that an N1 alkylated triazabutadiene molecule was stable in acidic conditions. However, alkylation of these compounds is effectively irreversible.

Inventors have surprisingly discovered that carboxylation on N1 of triazabutadienes reversibly yields stabilized or protected versions of triazabutadienes, e.g., pro-triazabutadienes that are generally stable in acidic conditions. For example, carboxylation on N1 yielded a pro-triazabutadiene molecule that is stable in concentrated HCl in methanol; treating the pro-triazabutadiene molecule with NaOH in methanol returned the original triazabutadiene molecule (which can then be degraded, e.g., in acidic conditions). Thus, the pro-triazabutadiene molecule may function as a means to protect triazabutadienes from degradation, e.g., under acidic conditions. In some cases the release of the triazabutadiene molecule from the pro-triazabutadiene molecule can be selectively triggered (under appropriate conditions), e.g., via enzymatic triggers. This can allow for many applications that could benefit from selective triazabutadiene activation.

As used herein, the terms "protected triazabutadiene," "releasable triazabutadiene" and "pro-triazabutadiene" refer to molecules that comprise an inactive form of a triazabutadiene molecule (e.g., a protected version of a triazabutadiene) but can yield or release an active triazabutadiene molecule (possibly further yielding an aryl diazonium species) upon appropriate conditions.

The present invention features triazabutadiene molecules, e.g., water-soluble triazabutadiene molecules. The present invention also features methods of use (applications) of said triazabutadiene molecules, methods of cleavage of said triazabutadiene molecules (e.g., decomposition in water, reductive cleavage, pH-dependent cleavage, light-catalyzed cleavage, etc.), and methods of synthesis of said triazabutadienes. For example, the present invention features methods and compositions for yielding an aryl diazonium species from a triazabutadiene molecule, e.g., a protected aryl diazonium species in the form of a triazabutadiene. In some embodiments, an enzyme catalyzes the reaction yielding the aryl diazonium species from the triazabutadiene molecule. The molecules of the present invention (and/or the products of triazabutadiene molecule cleavage (e.g., diazonium species) may be used for a variety of applications. For example, the pro-triazabutadiene molecules of the present invention may be used in drug delivery systems.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF SUMMARY OF THE INVENTION

The present invention features protected triazabutadienes (or pro-triazabutadienes) that release a triazabutadiene and a derivative of $Z^2$ (see below) when subjected to a trigger that results in deprotection of the N1 nitrogen. As used herein, the term N1 nitrogen refers to the nitrogen to which $Z^1$ and $Z^2$ are bonded (see below). For example, the present invention features compounds of Formula B:

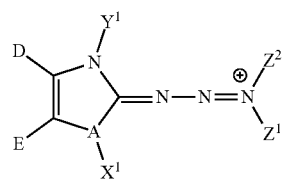

Formula B

In some embodiments, A is —N—. In some embodiments, D is —H. In some embodiments, E is —H.

In some embodiments, $X^1$ is an aryl, an alkyl, a carboxylic acid, an alcohol, or an amine. For example, in some embodiments, $X^1$ is methyl. In some embodiments, $X^1$ is t-butyl. In some embodiments, $X^1$ is a moiety conferring water solubility. In some embodiments, $X^1$ is a moiety conferring a particular pharmacokinetic property. In certain embodiments, $X^1$ is a moiety of the formula —$R^1$-$Q^1$. wherein $R^1$ is a $C_{1-6}$ alkylene, and $Q^1$ is a sulfate, phosphate, or a quaternary ammonium cation.

In some embodiments, $Y^1$ is an aryl, an alkyl, a carboxylic acid, an alcohol, or an amine. In some embodiments, $Y^1$ is methyl. In some embodiments, $Y^1$ is t-butyl. In some embodiments, $Y^1$ is one of the compounds shown in FIG. 14B. In certain embodiments, $Y^1$ is a NHS-ester moiety. In certain embodiments, $Y^1$ is an oligonucleotide. In certain embodiments, $Y^1$ is a peptide. In certain embodiments, $Y^1$ is a fluorescence quencher. In certain embodiments, $Y^1$ is a pro-fluorophore. In certain embodiments, $Y^1$ is an alkyne. In certain embodiments, $Y^1$ is a triazene. In certain embodiments, $Y^1$ is a tri-substituted aryl.

In some embodiments, $X^1$ and $Y^1$ are both alkyl. In some embodiments, $X^1$ and $Y^1$ are both methyl. In some embodiments, $X^1$ and $Y^1$ are both t-butyl. In certain embodiments, $X^1$ is a mesityl group. $Y^1$ is a mesityl group, or both $X^1$ and $Y^1$ are mesityl groups.

In some embodiments, $Z^1$ is an aryl. In certain embodiments, $Z^1$ is a drug with a phenolic functional group. In some embodiments, $Z^2$ is a moiety comprising a carbonyl group.

As a non-limiting example, in some embodiments, the compound is according to Formula B, wherein A is —N—; D is —H; E is —H; $Y^1$ is tBu; $X^1$ is Me; Z1 is aryl, e.g., with amide-linked alkyne or azide; and $Z^2$=COOEt.

In some embodiments, the compound of Formula B is incorporated into an amino acid.

The present invention also features methods of selectively activating a triazabutadiene. The method comprises introducing a trigger to a compound according to Formula B as describe above, wherein the trigger results in deprotection of N1 nitrogen to cause the compound to yield an active triazabutadiene molecule and a derivative of $Z^2$. In some embodiments, the derivative of $Z^2$ is a drug or a pro-drug. In some embodiments, the active triazabutadiene molecule yields an aryl diazonium species.

In some embodiments, the trigger is basic conditions. In some embodiments, the trigger is an enzyme, e.g., a phosphatase, a sulfatase, an esterase, a nitroreductase, etc. In some embodiments, the trigger is a redox environment, e.g., a redox environment inside a cell. In some embodiments, the trigger is light.

In some embodiments, the compound of Formula B is stable in acidic conditions. e.g., a solution having a pH of 8.0 or less, a solution having a pH of 7.0 or less, a solution having a pH of 6.0 or less, etc.

The present invention also features a method of drug release or cargo release. In certain embodiments, the method comprising introducing an enzymatic trigger to a pro-triazabutadiene molecule according to any the embodiments herein, wherein the enzymatic trigger causes deprotection of N1 nitrogen thereby causing release of a triazabutadiene molecule and a derivative of $Z^2$, wherein the derivative of $Z^2$ comprises a drug or a cargo. In certain embodiments, the cargo or drug is a pro-drug.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DETAILED DESCRIPTION OF THE INVENTION

I. Triazabutadiene Molecules

Figure 1:
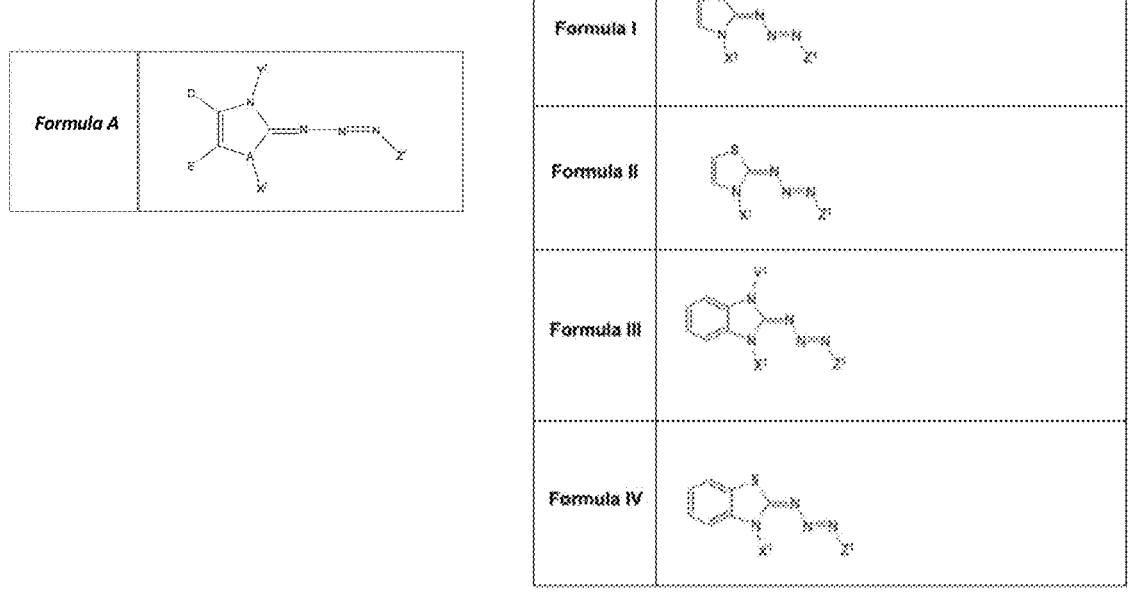
FIG. 1 shows non-limiting examples of triazabutadiene molecules.

The present invention features triazabutadiene molecules (e.g., water-soluble triazabutadienes). Non-limiting examples of formulas for triazabutadiene molecules of the present invention are of shown in FIG. 1. For example, in some embodiments, triazabutadienes are according to Formula A. Examples of Formula A are shown as Formula I, II, III, and IV. The present invention is not limited to Formula A, Formula I, Formula II, Formula III, and Formula IV. Referring to FIG. 1, in some embodiments, A=S, O, or N. (Note in some embodiments, if A=S, Y$^1$ and X$^1$ may be switched.) In some embodiments, D=H, —CH=CH—CH=E-, halides, cyano, sulfonates, alkyl chain, or trifluoromethyl. In some embodiments, E=H, —CH=CH—CH=D-, halides, cyano, sulfonates, alkyl chain, or trifluoromethyl.

In some embodiments, X$^1$ is a moiety conferring water solubility. In certain embodiments, Y$^1$ is a tri-substituted aryl, an alkyl, a carboxylic acid, an alcohol, or an amine (see also FIG. 14B). In some embodiments, Y$^1$ is a tri-substituted aryl group, the tri-substituted aryl group comprising a NHS-ester moiety (e.g., for protein linkage); an oligonucleotide; a peptide; a fluorescence quencher; a pro-fluorophore; an alkyne (e.g., for click chemistry); a triazene (e.g., from click reaction); the like; or a combination thereof. In some embodiments, Y$^1$ comprises an aldehyde; an amine (e.g., Fmoc protected), aminooxy, halogen (e.g., radio isotope); the like, or a combination thereof. In some embodiments, Z$^1$ is an aryl, e.g., a substituted aryl. In some embodiments, Z$^1$ comprises a NHS-ester moiety; an oligonucleotide; a peptide; a fluorescence quencher; a pro-fluorophore; a biologically active acid labile compound; a prodrug comprising a phenolic functional group; releasable cargo; an alkyne (e.g., for click chemistry); a triazene (e.g., from click reaction); the like, or a combination thereof. In some embodiments, Z$^1$ comprises an aldehyde; an amine (e.g., Fmoc protected), aminooxy, halogen (e.g., radio isotope); the like, or a combination thereof.

In some embodiments, X$^1$ may comprise a functional group that confers water solubility. In some embodiments, X$^1$ comprise a moiety of the formula —R$^1$-Q$^1$, wherein R$^1$ is C$_1$-6 alkylene, and Q$^1$ is sulfate, phosphate, or a quaternary ammonium cation. In some embodiments, X$^1$ is a moiety of the formula —R$^1$-Q$^1$, wherein R$^1$ is C$_{1-6}$ alkylene, and Q$^1$ is sulfate (e.g., —(O)$_n$SO$_3$R$^a$, where n is 0 or 1, and R$^a$ is C1-6 alkyl or typically H), phosphate (e.g., —(O)$_n$PO$_3$R$^a$, where n is 0 or 1, and R$^a$ is C1-6 alkyl or typically H), or a quaternary ammonium cation (e.g., —[NR$^a$R$^b$R$^c$]$^+$, where each of R$^a$, R$^b$, and R$^c$ is independently H or C$_{1-6}$ alkyl). As used herein, the term "alkyl" refers to a saturated linear monovalent hydrocarbon moiety of one to twelve, typically one to six, carbon atoms or a saturated branched monovalent hydrocarbon moiety of three to twelve, typically three to six, carbon atoms. Examples of alkyl groups include, but are not limited to, methyl, ethyl, n-propyl, 2-propyl, tert-butyl, pentyl, and the like. The term "alkene" refers to a saturated linear divalent hydrocarbon moiety of one to twelve, typically one to six, carbon atoms or a branched saturated divalent hydrocarbon moiety of three to twelve, typically three to six, carbon atoms. Examples of alkene groups include, but are not limited to, methylene, ethylene, propylene, butylene, pentylene, and the like.

Triazabutadiene molecules of the present invention may be readily soluble in water. In some embodiments, the solubility of the triazabutadiene molecule in water is at least 23 g/L of water (50 mM). In some embodiments, the triazabutadiene molecule is stable in pH 7.4 phosphate buffer. The phosphate buffer solutions are commercially available or can be prepared, for example, as described in http://cshprotocols.cshlp.org/content/2006/1/pdb.rec8247. In some instances, the half-life of the triazabutadiene molecules of the present invention in pH 7.4 phosphate buffer solution is at least 24 hours.

Stability of the triazabutadiene molecule may be measured in various ways. In some embodiments, stability is measured by the half-life of the molecule (or the half-life of the molecule in a particular buffer at a particular pH). In some embodiments, the molecule has a half-life of at least 12 hours in a pH 7.4 buffer. In some embodiments, the molecule has half-life of at least 24 hours in a pH 7.4 buffer. In some embodiments, the molecule has half-life of at least 36 hours in a pH 7.4 buffer. In some embodiments, the triazabutadiene molecule has a half-life of at least 8 hours, at least 10 hours, at least 12 hours, at least 20 hours, at least 24 hours, at least 30 hours, at least 36 hours, etc. The present invention is not limited to the aforementioned examples of stability measurements.

Without wishing to limit the present invention to any theory or mechanism, it is believed that the triazabutadiene molecules of the present invention are advantageous because the triazabutadiene molecules can be easily modified (e.g., various different functional groups can be easily used as $X^1$, $Y^1$, or $Z^1$ (see FIG. 1). And, the release of the diazonium species following triazabutadiene molecule breakdown (via certain mechanisms, as described below) may provide a new functional group that can be taken advantage of in various applications. Also, it may be considered advantageous that the breakdown of the triazabutadiene molecule is irreversible.

II. Cleavage of Triazabutadiene Molecules a. Water and/or Low pH

Figure 2A:
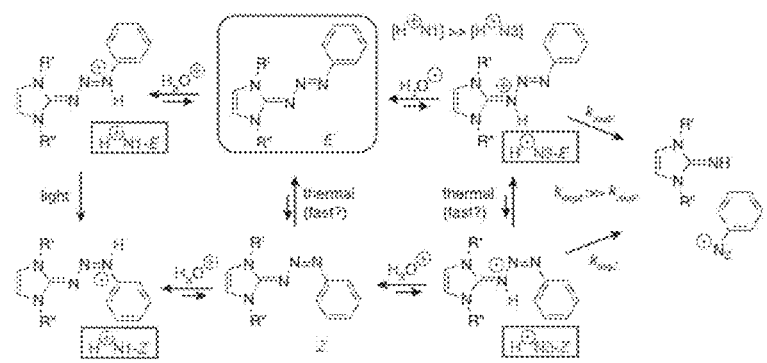
FIG. 2A shows triazabutadiene molecules undergoing decomposition to diazonium salts (and cyclic guanidine species). Note the reaction/equilibrium arrows are not to scale.

The present invention shows that triazabutadiene molecules may break down in the presence of water to generate reactive aryl diazonium compounds. For example, FIG. 2A shows that triazabutadiene molecules of the present invention can undergo decomposition to diazonium salts (reactive aryl diazonium compounds) and cyclic guanidine species. Aryl diazonium compounds may react with electron-rich aryl rings (e.g., aryl species wherein the bond of interest is a nitrogen-carbon bond; indoles, anilines, phenol-containing compounds such as resorcinol or tyrosine, etc.) to form stable azobenzene linkages (e.g., an aryl azo dye, e.g., Sudan Orange). (Note the present invention is not limited to the aforementioned phenol-containing species. In some embodiments, imidazole compounds (e.g., purine bases like guanine) may be used in lieu of a phenol-containing compound.) The diazonium species may not necessarily react with an electron-rich aryl rings compound (e.g., phenol species), for example if a phenol species is not present. The diazonium species may irreversibly extrude nitrogen gas to generate an aryl cation, which will rapidly be quenched by solvating water, thus synthesizing a new phenolic compound (e.g., HO-Ph, wherein Ph refers to the phenyl ring); thus, the diazonium portion of the triazabutadiene molecule may function as a masked hydroxyl group.

Figure 2B:
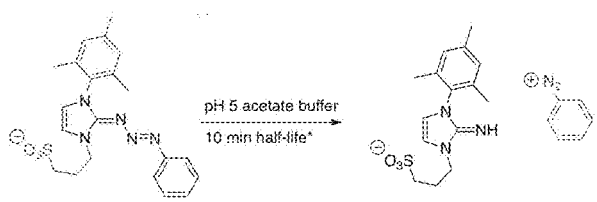
FIG. 2B shows a triazabutadiene molecule breaking down (in low pH conditions) to a diazonium species and a cyclic guanidine species.

In some embodiments, the triazabutadiene molecules are acid labile, e.g., unstable at particular pH levels (see FIG. 2B). For example, decreases in pH may increase the rate at which the triazabutadiene molecules break down (the half life of the molecule decreases). In some embodiments, the triazabutadiene molecules are unstable at low (lowered) pH levels (e.g., lowered pH as compared to a particular pH that the molecule may be stored at, e.g., a pH wherein the molecule has a particular desired half life). Low pH levels, in some example, may be a sub-physiological pH (7.4 or less). In some embodiments, the triazabutadiene molecules are (more) unstable at pH 7.0 or less, pH 6.8 or less, pH 6.5 or less, pH 6.2 or less, pH 6.0 or less. pH 5.8 or less, pH 5.6 or less, pH 5.5 or less, pH 5.2 or less, pH 5.0 or less, etc.

The term 'low pH" may refer to several different pH levels. Since the functional groups attached to the molecule (e.g., see $X^1$, $Y^1$, $Z^1$ of Formula I) affect the stability of the molecule (as well as water solubility), the pH that is necessary to increase the rate of breakdown of the triazabutadiene molecule (e.g., the "lowered pH") may be different for different molecules. In some embodiments, the low pH is a pH of 7.4 or less, 7.2 or less, 7.0 or less, etc. In some embodiments, the low pH is a pH of 6.8 or less, 6.6 or less, 6.5 or less, 6.4 or less, 6.2 or less, 6.0 or less, etc. In some embodiments, the low pH is a pH of 5.8, 5.5 or less, 5.0 or less, etc.

In some embodiments, the triazabutadiene molecules can break down without the presence of the low pH (the molecules have half lives); however, in some embodiments, a lowered pH enhances the reaction (e.g., increases the rate of reaction). As such, a low pH may or may not be used with the molecules and/or methods of the present invention. In some embodiments, the triazabutadiene molecule has a half-life of no more than 1 hour in a pH 7.4 aqueous solution. In some embodiments, the triazabutadiene molecule has a half-life of no more than 30 minutes in a pH 7.4 aqueous solution. In some embodiments, the triazabutadiene molecule has a half-life of no more than 15 minutes in a pH 7.4 aqueous solution.

The present invention also features methods of breaking down triazabutadiene molecules. In some embodiments, the method comprises subjecting the molecule to water. In some embodiments, the method comprises subjecting the molecule to a low pH (e.g., a low pH that is appropriate for the molecule, e.g., a lowered pH that increases the rate at which the triazabutadiene molecule breaks down).

In some embodiments, the reaction of the triazabutadiene molecule to the diazonium species occurs in water within 10-30 seconds. In some embodiments, the reaction of the triazabutadiene molecule to the diazonium species occurs in water within 30 seconds to 1 minute. In some embodiments, the reaction of the triazabutadiene molecule to the diazonium species occurs in water within 1 to 5 minutes. In some embodiments, the reaction of the triazabutadiene molecule to the diazonium species occurs in water within 5-10 minutes. In some embodiments, the reaction of the triazabutadiene molecule to the diazonium species occurs in water within 10-15 minutes. In some embodiments, the reaction of the triazabutadiene molecule to the diazonium species occurs in water within 15-20 minutes. In some embodiments, the reaction of the triazabutadiene molecule to the diazonium species occurs in water within 25 minutes, within 30 minutes, within 45 minutes, or within 60 minutes.

In some embodiments, the diazonium species may be visually differentiated from the triazabutadiene species, e.g., the diazonium species is visually distinct (e.g., a different color) from the triazabutadiene molecule. If applicable, in some embodiments, the aryl azo dye may be visually differentiated from the triazabutadiene species and the diazonium species, e.g., the aryl azo dye is visually distinct (e.g., a different color) from the triazabutadiene species and the diazonium species.

Given the possibility that the aryl azo dye is visually distinct from the triazabutadiene molecule (and/or the diazonium species), the present invention also features methods of producing a visually detectable molecule. In some embodiments, the method comprises providing a triazabutadiene molecule according to the present invention and subjecting the triazabutadiene molecule to water and/or a low pH (or light as discussed below, or light and low pH, etc.). The low pH (or light, or light and low pH, etc.) initiates (e.g., increases the rate of) the irreversible reaction to produce the diazonium species and the cyclic guanidine species. As previously discussed, the diazonium species may be visually distinct from the triazabutadiene molecule; therefore the reaction produces a visually detectable molecule.

b. Reductive Cleavage

Figure 3:
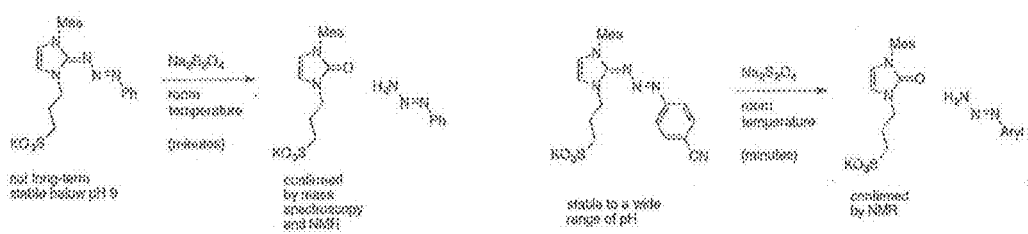
FIG. 3 shows reductive cleavage of triazabutadiene molecules.

Other mechanisms may be used to break down triazabutadiene molecules of the present invention. For example, in some embodiments, reducing conditions increase the rate at which the triazabutadiene molecules break down. Thus, the present invention also features methods of reductive cleavage of triazabutadiene molecules. For example, triazabutadiene molecules (e.g., triazabutadiene scaffolds) may be readily cleaved using reducing agents such as but not limited to sodium dithionite (sodium hydrosulfite) ($Na_2S_2O_4$) (see FIG. 3). In some embodiments, the reducing agent comprises lithium aluminum hydride, sodium borohydride, or the like.

In some embodiments, electrochemical reduction may be used in accordance with the present invention. Reductive cleavage of the triazabutadiene molecules provides a urea functionality and a terminal aryl triazene. In some embodiments, the aryl triazene is further reduced in the presence of excess reducing agent (e.g., sodium dithionite). In some embodiments, the reduction can be observed visually by the change in color of a solution. For example, there may be a subtle change of yellows that results from a loss of a shoulder in UV/vis spectrum.

In some embodiments, the ratio of the concentration of the triazabutadiene to the reducing agent is about 1:1. In some embodiments, the ratio of the concentration of the triazabutadiene to the reducing agent is about 1:2. The present invention is not limited to the aforementioned ratios. For example, in some embodiments, the ratio of the concentration of the triazabutadiene to the reducing agent is about 2:3, 4:5, etc. The present invention is not limited to the aforementioned ratio of concentrations.

In some embodiments, the reduction can occur within about 10 minutes, within about 15 minutes, within about 20 minutes, within about 25 min, within about 30 min, etc., at room temperature. Without wishing to limit the present invention to any theory or mechanism, it is believed that reductive cleavage of the triazabutadiene molecules is advantageous because it can occur rapidly (e.g., within 10 minutes, within 15 minutes). Also, the triazabutadiene molecules that are highly stable in acid (e.g., a p-CN derived triazabutadiene) may still be susceptible to reducing conditions.

In some embodiments, reductive cleavage of triazabutadiene molecules may also be used to cleave unreacted triazabutadienes that did not undergo diazonium formation/reaction chemistry that is associated with a drop in pH (or other mechanism) as described above (a sort of quench for the pH chemistry).

c. Light-Initiated Cleavage

Figure 4A:
FIG. 4A shows light catalyzed cleavage of triazabutadiene molecules.
Figure 4A:
Figure 4B:
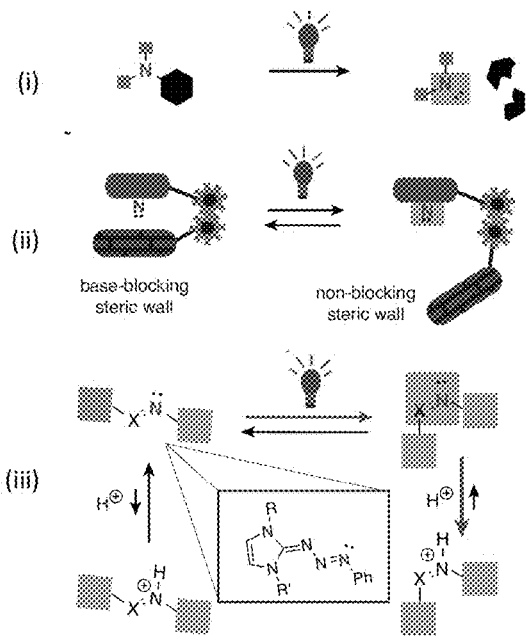
FIG. 4B shows photochemically generated bases. (i) A masked base may decompose to reveal a basic nitrogen atom upon exposure to light; (ii) The basic nitrogen atom of a molecule obscured by a steric wall may be reversibly swung away in a photochemically triggered fashion; (iii) The intrinsic basicity of a nitrogen-containing functional group may be altered by a photochemical event.

In some embodiments, light increases the rate at which the triazabutadiene molecule breaks down (into the cyclic guanidine species and the diazonium species) (see FIG. 4A). The present invention also features water-soluble triazabutadienes that, upon photo-irradiation, may be rendered more basic in a reversible fashion. Referring to FIG. 4B, for reference, a protecting group of a masked base may decompose to reveal a basic nitrogen atom upon exposure to light. Or, a basic nitrogen atom of a molecule obscured by a steric wall may be reversibly swung away in a photochemically-triggered manner. The present invention shows the intrinsic basicity of a nitrogen-containing functional group may be altered by a photochemical event.

Figure 5A:
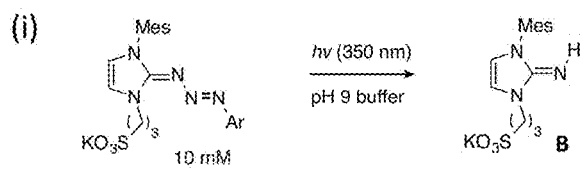
FIG. 5A shows time-dependent photo-induced degradation of triazabutadienes. (i) The reaction was monitored by comparing starting materials (A, C, D, and E) with product (B); (ii) Peak absorption and extinction coefficients for all of the compounds were excitable by the UV source used; (iii) Time-dependent conversion of compounds was measured by NMR integration.
Figure 5A:
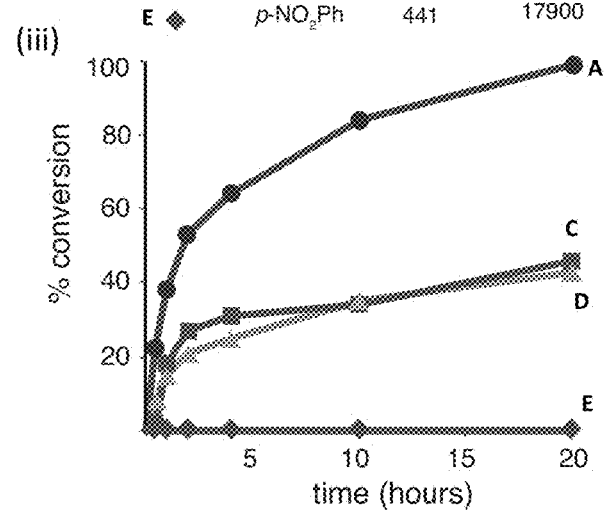

Referring to FIG. 5A, in some embodiments, triazabutadiene molecules of the present invention may readily photoisomerize to a more reactive Z-form. As an example, an aqueous solution of Compound A was irradiated with a simple hand-held UV lamp ("365 nm," measured at 350 nm). Consumption of Compound A was observed after only a few hours. The non-irradiated reaction under similar conditions was stable for days as partial degradation rapidly rendered the solution mildly basic. Without wishing to limit the present invention to any theory or mechanism, it was hypothesized that if a two-electron process were happening, then Compound A-Z would be more basic than Compound A-E. A 1.0 N NaOH solution of Compound A was treated with light. At pH 14, Compound A was stable for weeks in the dark; it was surprisingly discovered that near complete consumption of starting material after 20 hours of constant irradiation occurred. NMR analysis of samples post-irradiation showed cyclic guanidine Compound B. Evidence of a benzene diazonium species or phenol/azobenzene products derived therefrom was not observed. Benzene diazonium ions also absorb UV light to expel nitrogen and generate a benzene radical. In order to resolve if the initial cleavage undergoes a radical homolytic mechanism versus a two-electron heterolytic mechanism, a trapping experiment using resorcinol was conducted. (Resorcinol was chosen because it can serve a dual role as a radical scavenger and a trap benzene diazonium species that could be formed.) An excess of resorcinol was added to a pH 9 borate-buffered solution of Compound A and the mixture was irradiated with light. The known azobenzene, Sudan Orange G, was formed in a 65% yield (versus 4% for the non-irradiated reaction). Derivatives of Compound A were made to examine the effects of electronic perturbations on the light-induced degradation. Electron deficient aryl rings are more stable at lower pH, and this trend generally holds true for the photochemical reactions as well. A buffered borate solution was chosen due to its alkaline nature and lack of complicating signals in the NMR experiment. Compounds C-E all have absorption spectra that are well within the range of the UV lamp (see FIG. 5A(ii)). Both m-$NO_2$ (Compound C) and p-CN (Compound D) had similar rates of reaction, both slower than Compound A. To rule out other effects associated with possible heating or interactions of the buffer, p-$NO_2$ derivative Compound E was irradiated because of its significantly red-shifted spectrum. Compound E absorbed in a range that was not irradiated with the UV lamp and as such was recalcitrant to degradation (see FIG. 5A(iii)).

As previously discussed, poorly (or non-) buffered aqueous solutions could become more basic as a function of time due to the degradation to Compound B and the aryl diazonium species. Without wishing to limit the present invention to any theory or mechanism, it is believed that the cause of the increase in pH is Compound B, which acts as a base. It was found that reactions slowed and eventually stopped once the pH had risen to around 9. Without wishing to limit the present invention to any theory or mechanism, it was hypothesized that by driving the reaction to completion with light, it would be possible to increase the pH beyond this dark-reaction imposed wall (analogous FIG. 4B(ii)). Using NMR and a pH meter, it was observed that the pH of a solution of Compound A irradiated with UV light rose in a time-dependent manner.

In an effort to examine the rate order for the pH-increasing reaction more carefully, in situ, real-time pH measurements were acquired. Compound A was dissolved in water and the pH of the solution was adjusted to 9 such that it would not form Compound B in the absence of light. Upon exposing the solution to 350 nm light, it was surprisingly discovered that the solution rapidly spiked up to a pH of ~10 over the course of several minutes, and only upon much longer exposure slowly became more basic. This spike was not at all consistent with the model of the pH increase being solely linked to the concentration of Compound B being generated. Moreover, previous NMR studies showed that much more time was required to afford a pH change commensurate with this apparent level of degradation.

Figure 5B:
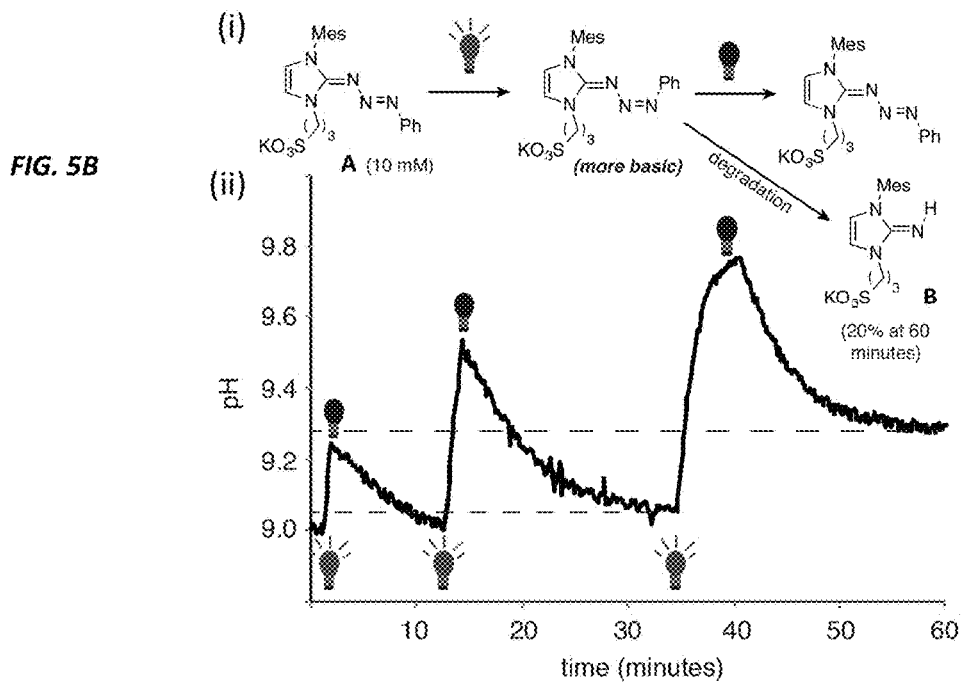
FIG. 5B shows (i) Compound A is rendered more basic upon exposure to light; that basicity recovers (to some extent) in the absence of light; (ii) Oscillating UV irradiation provides a saw-tooth pH trend over time.

Without wishing to limit the present invention to any theory or mechanism, it was hypothesized that the rapid pH increase that was observed was not attributed to Compound B, but instead a result of the Z isomer being significantly more basic than the E isomer (see FIG. 5B(i)). A sample was irradiated and then the light was turned off once the pH of the solution started to increase noticeably. As the sample thermally reverted to the more stable E form, the pH of the solution dropped as well (see FIG. 5B(ii)). The experiment was repeated with increasing times of irradiation, and a saw-tooth pattern was obtained. The process was not completely reversible due to some degradation to Compound B. Indeed, triazabutadiene Compound A can serve a dual role of being a photo-masked base (see FIG. 4B(i)), and a base whose intrinsic functional group properties are altered photochemically (FIG. 4B(iii)).

Figure 5C:
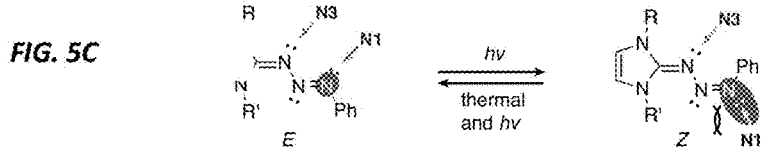
FIG. 5C shows the lone-pair of electrons on the N1 nitrogen atom becomes more electron-rich upon isomerization from E to Z.

This phenomenon via an isomerization-induced $pK_b$ change was surprisingly discovered by the inventor. Without wishing to limit the present invention to any theory or mechanism, unlike the case where Hecht's compound is rendered basic upon irradiation by way of moving of a steric wall (see FIG. 4B(ii)), it may be unlikely that steric factors play a significant role in this chemistry, e.g., in water. It is possible that the E isomer has alternating non-π involved lone pairs of electrons, whereas the Z isomer has two adjacent lone pairs of electrons (see FIG. 5C). The electronic repulsion from these renders N1 much more electron rich, and thus a stronger Lewis base.

Referring to FIG. 5A(iii), Compound C and Compound D were examined in an effort to find a base that was reversibly basic but also more resistant to degradation. In both cases, a slow subtle change to the pH was observed, but none as dramatic and rapid as Compound A. Without wishing to limit the present invention to any theory or mechanism, it is believed that this may be due to factors such as (a) faster thermal isomerization to the E isomer such that a build up of the Z isomer is not possible; (b) the electron-deficient triazabutadienes are less basic to begin with, so a transition is not observable in the operating pH range.

It is possible that Compound A may be useful as a photo-catalytic base in the context of organic reactions. With limited solubility in all but DMSO, the stability of Compound A was tested. As noted previously, Compound A is quite stable to an excess of acetic acid in DMSO, showing only 12% degradation over 14 hours at room temperature. Upon irradiation with light, Compound A in presence of acetic acid completely fell apart over the same time frame. To confirm that this was due to the acid, a solution of Compound A (in pure DMSO) was irradiated. After four hours of constant irradiation in acid-free DMSO, an E:Z ratio of nearly 50:50 was observed. Moreover, unlike in water, the thermal reversion from Z to E is slow in pure DMSO with a half-life on the order of days. Attributing this to lack of protonation, a control in MeOD was run, and a first-order thermal isomerization was observed with a rate of $3 \times 10^{-5}$ s$^{-1}$ ($t_{1/2}$~6.4 hours), in addition to some degradation to Compound B.

Figure 5D:
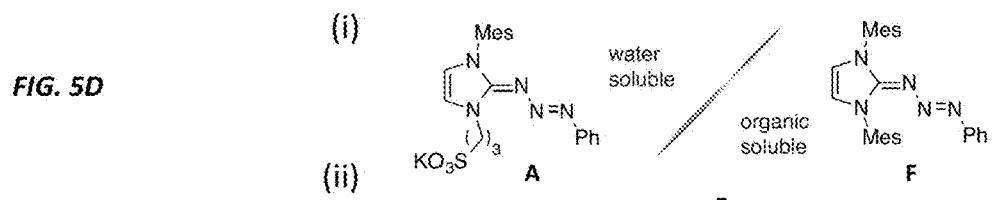
FIG. 5D shows the use of the photobase as a catalyst (i) Structures of water-soluble Compound A versus organic soluble Compound F; (ii) The Henry reaction between Compound G and Compound H was carried out at room temperature and varying amounts of catalyst; (iii) The reactions were monitored by ReactIR™, following consumption of aldehyde Compound H.
Figure 5D:
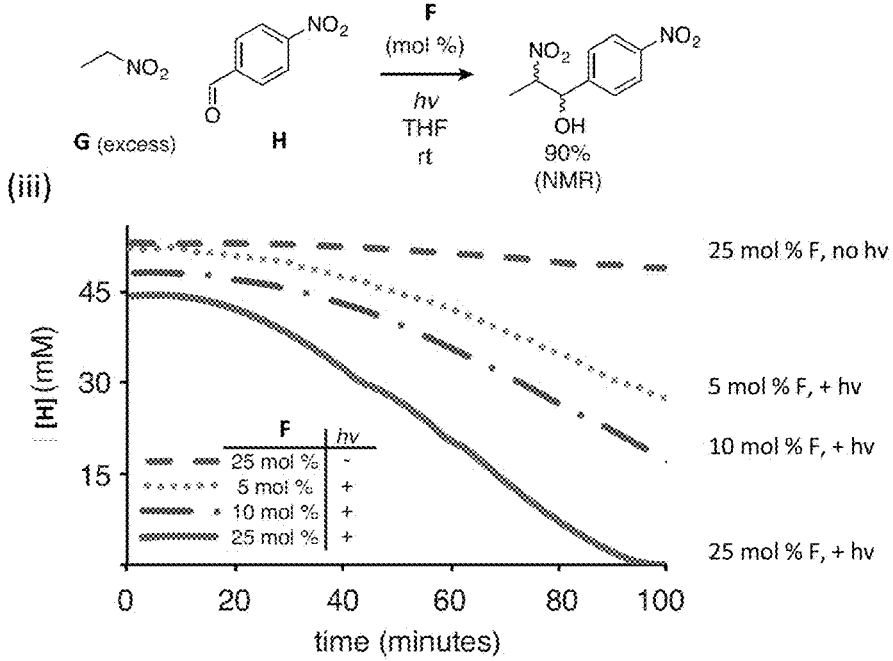

Referring to FIG. 5D, due to the limited organic solubility of Compound A, Compound F (FIG. 5D(i)) was synthesized. With Compound F, a similar light-induced acid sensitivity was observed in DMSO (and slow thermal isomerization). Based on the apparent $pK_b$ of Compound F, $pK_a$ were matched to condensation substrates. A Henry reaction between nitroethane (Compound G) and p-nitrobenzaldehyde (H) was chosen to demonstrate the virtues of Compound F (FIG. 5D(ii)). The reaction between Compound G and Compound H occurred rapidly at room temperature in a light and catalyst dependent manner (FIG. 5D(iii)). The reaction with 25 mole % Compound F in the absence of light was exceedingly slow. Likewise, the reaction with light but no catalyst also failed to proceed. The cyclic guanidine was not observed during a post-reaction analysis of the components from a 25 mole % Compound F run, indicating that the Z-isomer of Compound F is likely to be the catalytically active species in solution. Slow thermal isomerization back to the E-isomer in aprotic organic solvents together with a fast overall reaction attempts to adjust the reaction rate prior to consumption of Compound H. Interestingly, the reaction catalyzed with Compound F was significantly faster than the same reaction reported by Hecht. This may provide evidence that Compound F-Z is more basic than Hecht's blocked trialkylamine.

As previously discussed, the present invention features methods of breaking down triazabutadiene molecules by subjecting the molecule to light. The light may, for example, include wavelengths of about 400 nm. The present invention is not limited to wavelengths of 400 nm or about 400 nm. For example, in some embodiments, the wavelength is from 350 nm to 400 nm (e.g., 370 nm). In some embodiments, the wavelength is from 360 nm to 410 nm. In some embodiments, the wavelength is from 330 nm to 420 nm. In some embodiments, the wavelength is from 340 nm to 430 nm. In some embodiments, the method comprises subjecting the molecule to a low pH and to light.

Figure 6A:
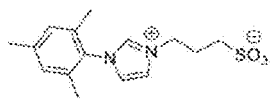
FIG. 6A-FIG. 6H show non-limiting examples of triazabutadienes or reaction schemes involving triazabutadienes.
Figure 6B:
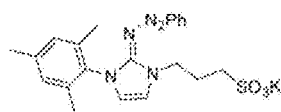

As previously discussed, light-promoted reactivity and light-facilitating E/Z isomerization has been observed. In some embodiments, a system such as a UV-LED pen may be used for these reactions, however the present invention is not limited to a UV-LED pen and may utilize any appropriate system. The UV-LED pens may allow for relatively narrow bandwidth irradiation of these compounds (but are not limited to these bandwidths). The color of the bulk material shifts as a result of electronic perturbations to the aryl azide starting material. For example, nitro derivative Compound 6e of FIG. 6G (described below) is rust-red, versus an orange phenyl Compound 6c of FIG. 6F (described below) and yellow-orange methoxy Compound 6d of FIG. 6G (described below). It may be possible for selective irradiation of a complex mixture in an orthogonal sense. These experiments may be performed in basic aqueous solutions to maintain the solvation properties of water while also preventing the degradation pathway stemming from protonation. These experiments are not limited to basic aqueous solutions.

Without wishing to limit the present invention to any theory or mechanism, it may be considered advantageous that the breakdown of the triazabutadiene molecule is irreversible.

III. Synthesis of Water-Soluable Triazabutadiene Molecules and Experimental Examples Synthesis of 1-mesityl-1-H-imidazole: To a solution of 2,4,6-trimethylaniline (1.35 g, 10.0 mmol) in methanol (15 mL) □was added a solution of glyoxal (40%) (1.14 mL, 40% in water, 10. mmol). The mixture was stirred at room temperature until a solid formed. Thereafter, solid ammonium chloride (1.07 g, 20 mmol), formaldehyde (37%) (1.6 mL 37% in water, 60. mmol) and methanol (40 mL) were added, and the mixture was heated to reflux for one hour. After the hour, phosphoric acid (1.4 ml of an 85% solution) was added drop wise and the mixture was refluxed for an additional eight hours. Upon cooling to room temperature ice (30 g) was added and the solution was brought to a pH of 9 with potassium hydroxide (40% in water). The following mixture was extracted repeatedly with diethyl ether. The ether phase was dried over magnesium sulfate and solvent removed in vacuo to form a brown solid which was filtered and washed with hexanes to give the product (0.785 g; 42%). 1H NMR (500 MHz, CDCl3): δ 7.45 (t, J=1.1 Hz, 1H), 7.25 (t, J=1.1 Hz, 1H), 6.99 (dp, J=1.3, 0.7 Hz, 2H), 6.91 (t, J=1.3 Hz, 1H), 2.36 (t, J=0.7 Hz, 3H), 2.01 (t, J=0.6 Hz, 6H). 13C NMR (126 MHz, CDCl3) δ 138.80, 137.47, 135.42, 133.40, 129.55, 128.96, 120.02, 21.03, 17.33 (see Liu, J. et al. Synthesis 2003, 17, 2661-2666).

Synthesis of 3-(1-mesityl-1H-imidazol-3-ium-3-yl) propane-1-sulfonate (e.g., see FIG. 5A): To a solution of 1-mesityl-1-H-imidazole (1.00 g, 5.36 mmol) in toluene (30 mL) was added 1,3-propanesultone (1.00 g, 8.18 mmol) and the mixture was heated to reflux overnight. The mixture was allowed to cool to room temperature and the off-white precipitate collected by filtration. The precipitate was further washed with diethyl ether and dried using a vacuum oven to yield a solid (1.40 g; 84%). 1H NMR (500 MHz, D2O): δ 8.92 (t, J=1.6 Hz, 1H), 7.75 (t, J=1.8 Hz, 1H). 7.49 (t, J=1.8 Hz, 1H). 7.06 (q, J=0.8 Hz, 2H), 4.44 (t, J=7.1 Hz, 2H), 2.39-2.31 (m, 2H), 2.25 (s, 3H), 1.96 (s, 6H). 13C NMR (126 MHz, D2O) δ 141.42, 136.54, 134.64, 130.74, 124.34, 123.00, 48.18, 47.17, 25.03, 20.17, 16.29.

Synthesis of Potassium 3-(3-mesityl-2-(phenyltriaz-2-en-1-ylidene)-2, 3-dihydro-1H-imidazol-1-yl) propane-1-sulfonate (e.g., see FIG. 6B): To a slurry of 3-(1-mesityl-1H-imidazol-3-ium-3-yl)propane-1-sulfonate (50 mg, 0.16 mmol) in dry THF (6 mL), was added a solution of phenyl azide in THF (0.16 mL, 1 M, 0.16 mmol). To the solution was added KO-t-Bu (24 mg, 0.21 mmol) in one portion and the resulting mixture was stirred under argon for 4 hours. Hexanes (1 mL) was then added and the reaction mixture was filtered. The solvent was removed and the residue taken up in a minimal amount of DCM and on trituration with hexanes, pure product was obtained by filtration as a yellow powder (61 mg, 81%). 1H NMR (500 MHz, DMSO-d6) δ 7.32 (d, J=2.4 Hz, 1H), 7.07-7.02 (m, 4H), 6.99-6.94 (m, 1H), 6.84 (d, J=2.4 Hz, 1H), 6.51-6.47 (m, 2H), 4.09 (t, J=7.1 Hz, 2H), 2.34 (s, 3H), 2.12-2.04 (m, 2H), 1.95 (s, 6H). 13C NMR (126 MHz, DMSO-d6) δ 152.19, 151.13, 137.94, 136.15, 134.31, 129.31, 128.60, 125.26, 120.90, 117.61, 117.24, 48.52, 45.05, 25.80, 21.06, 17.95.

Using the procedures described herein, the p-methoxy and p-nitro analogs (from the p-MeO aryl azide and p-NO2 aryl azide) were also prepared.

For decomposition experiments, buffers were made to the appropriate pH in a 9:1 mix of H2O:D2O. These solutions were added to the compound being assayed such that the buffer capacity was at least 10 fold the concentration of the compound. Some experiments used 5 mg compound in 0.5 mL of buffer (e.g., pH 5 acetate buffer at 25 degrees C.). These were immediately inserted into an NMR instrument and scans were taken at even time intervals to calculate the half-life of the compound based on integration.

Figure 6C:
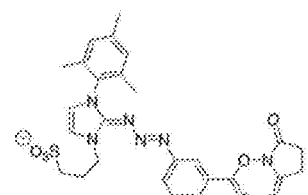
Figure 6D:
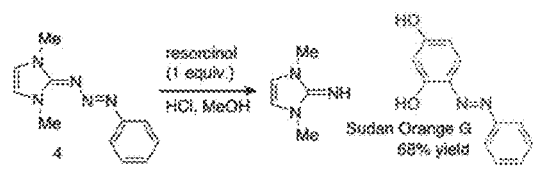

As another non-limiting example, an azide (e.g., NHS-azide) to N-heterocyclic carbene (NHC) route may be used to synthesize triazabutadiene molecules (e.g., see FIG. 6C). For example, as shown in Compound 4 of FIG. 6D, a triazabutadiene molecule was synthesized from dimethyl imidazole derived NHC and phenyl azide. When the triazabutadiene molecule (Compound 4) was treated with methanolic HCL, a rapid color change occurred. This change was confirmed to coincide with diazonium formation by trapping the reactive species with resorcinol to provide known diazo dye Sudan Orange G. When the triazabutadiene molecule (Compound 4) was treated with the much less acidic acetic acid, the same product was obtained. Compound 4 was not water-soluble.

Figure 6E:
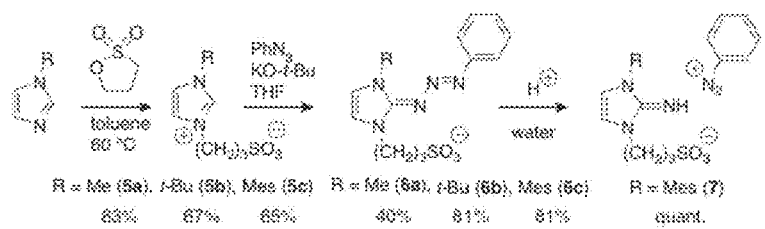
Figure 6F:
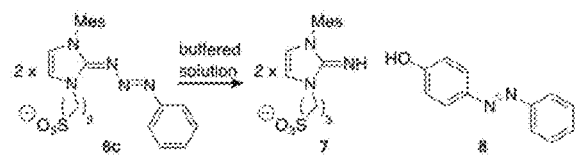

To render the triazabutadiene water-soluble, methyl imidazole was alkylated with propane sultone to provide the Zwitterionic NHC precursor Compound 5a (see FIG. 6E). Formation of the NHC under basic conditions in the presence of phenyl azide yielded the highly water soluble Compound 6a (see FIG. 6E). Compound 6a was highly colored, so its pH dependence was studied using UV/Vis. The reactions were not only pH-, but also scan-frequency dependent. Upon finding this, the stability of Compound 6a was studied in D2O in the dark using NMR. Even in the dark it was unstable, but not in the diazonium-forming way. Both Compound 6b and a more hindered mesityl (Mes) substituted Compound 6c (see FIG. 6E) were synthesized to stabilize what was initially considered to be a rearrangement pathway that could be blocked by steric repulsion. Compound 6c was the most stable of the three (less than 10% consumed after 24 hours versus 50% for Compound 6a and Compound 6b). Dissolution in 0.1 N NaOH rendered all compounds stable (e.g., no detectable degradation after 24 hours in the dark).

As mentioned above, Compound 6c was reasonably stable in pure D2O. Upon adjusting the pH to 5 with HCl, a rapid initial consumption of Compound 6c to Compound 7 (see FIG. 6E) and a benzenediazonium salt was noted. After this initial burst of reactivity, a slowing and apparent arresting of the reaction was noted. At this pH the hydronium was the limiting reagent. All future reactions were run in buffers with a buffer capacity sufficient to maintain a large excess of hydronium ions. The experiments were performed in 90:10 H2O:D2O buffered solutions to minimize considerations of pH vs. pD. The decomposition to diazonium salts and Compound 7 was measured as a function of pH in phosphate/citrate buffers from pH 4-7 and in a phosphate buffer from pH 6-8. All runs provided linear correlations of concentration and time, indicating a pseudo-zero order reaction (first order with respect to hydronium ion with a large excess of hydronium ions). While the peaks for Compound 7 remained constant, the peaks associated with Compound 6c drifted downfield as the reaction progressed. This drifting was highly reproducible across samples and buffers, but the underlying cause is not understood at this time. A sigmoidal correlation between rate and buffer pH centered at pH 6 was obtained. When resorcinol was not added to consume the diazonium species, 4-phenylazophenol (Compound 8) was observed (see FIG. 6F). Compound 8 came from the decomposition of one diazonium ion to phenol followed by reaction with a second diazonium ion. The instability of Compound 6c in a pH 7 phosphate buffer was surprising given the stability in D2O. Compound 6c was tested in a non-buffered 90:10 H2O:D2O solution and observed only >7% after 6 hours.

Figure 6G:
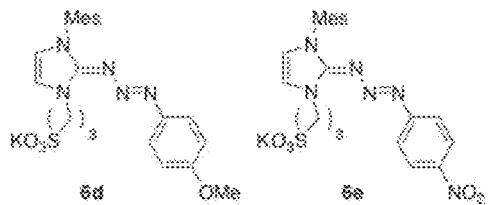

To further examine the reactivity of this class of compounds, variants Compound 6d and Compound 6e were synthesized (see FIG. 6G). It was hypothesized that the p-methoxy and p-nitro analogs (Compound 6d and Compound 6e, respectively) would display different reactivity profiles. It was observed that in pure D20, 26% of Compound 6d was consumed after 24 hours in the dark at room temperature as compared with Compound 6e, which was stable to within the detection limit of NMR. Preliminary data shows that Compound 6d undergoes decomposition to the diazonium species more rapidly than Compound 6c in pH 5, 6, and 7 phosphate/citrate buffer (rates of 2.0×10-5, 1.0×10-5, and 0.53×10-5 M/s, respectively). Upon attempting the same study with Compound 6e it rapidly precipitated out of solution across the same pH range. After collecting the precipitate and dissolving it in deuterated methanol, no change was observed from a sample of Compound 6e that had never been exposed to a buffered solution. Treatment of this methanolic Compound 6e with HCl led to an immediate color change and diazonium formation was confirmed by trapping with resorcinol. It is possible that 1) that the sodium salt of Compound 6e is much less soluble than the potassium salt; or 2) with different solvating ions present the sulfonate interacts with the electron-poor N2 nitrogen atom of the triazabutadiene to break conjugation and form an insoluble complex (this is backed by a reversible color change of the starting rust-red solid, to the light yellow precipitate). Note that the p-nitrobenzenediazonium salts are reported to have the best labeling efficiency of tyrosine residues on proteins.

The influence of solvated ions on reactivity was studied. In water, or a heavy water/water mixture, a near-zero rate of diazonium salt formation was observed, yet in solutions buffered to pH 7 and even pH 7.4, an increase in the reaction rate was observed. To assess the role of the anionic component, the reaction in the presence of a range of buffers while holding the pH constant may be observed. Buffers include but are not limited to those expected to have the most diverse properties, e.g., MES, a Zwitterionic morpholino sulfonic acid, and imidazolium chloride, the conjugate acid of a mild base, can both buffer a solution at pH 6.5, but ionic species in solution would be dramatically different. The metals in solution could well be acting as Lewis acids to activate our molecule. A range of metal halide salts dissolved in pure water at varying concentrations may be screened.

Figure 6H:
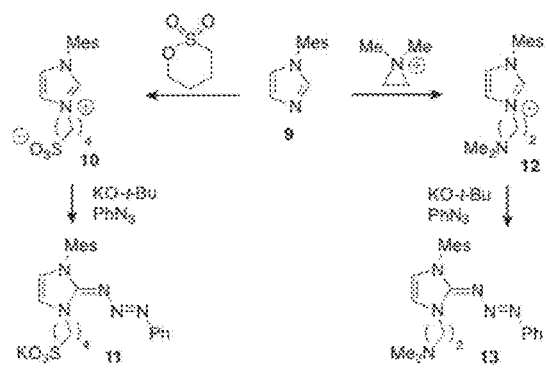

Note that all of the compounds in the 6 series (FIG. 6E, FIG. 6F, and FIG. 6G) have a built-in sulfonate to confer solubility. It is possible that this functional group could be serving an important role by effecting the localization of metals, directing them to interact with the nitrogen atoms of the triazabutadiene and thus alter the reactivity of the compound. This may be happening with Compound 6e to such an extreme that the compound is no longer soluble. This concept of a directed metal binding on triazabutadienes was observed, albeit in an organic environment. Referring to FIG. 6H, to study the role of the side chain, the imidazole core will be alkylated (Compound 9) with either butane sultone to provide imidazolium (Compound 10) and triazabutadiene (Compound 11), or a dialkyl aziridinium salt to provide the analogous Compound 12 and Compound 13 which invert the expected charge on the side-chain. The extra methylene in Compound 11 as compared with Compound 6 may alter the way that the side-chain bites back on the triazabutadiene. The tertiary amine will be protonated at physiological pH and as serve to invert the charge of the side arm. Without wishing to limit the present invention to any theory or mechanism, a potential bonus of Compound 13 is that the basic nitrogen may help localize this compound in the most acidic subcellular compartments much like LysoTracker™ dyes.

Regarding the role of mesityl group in reactivity, it is possible that a function of the mesityl in triazabutadiene reactivity is to provide a steric wall to prevent side reactions. The NMR of Compound 6c (see FIG. 6F) shows a tale of two hydrogen atoms on the imidazole ring. Without wishing to limit the present invention to any theory or mechanism, it is believed that because the ortho methyl groups prevent coplanar aryl rings, the mesityl group is unlikely to sit in conjugation with the imidazole, but the highly differentiated chemical environments might be explained by: 1) the mesityl Tr-system deshielding the adjacent hydrogen atom, and 2) the aryl ring having an inductive effect. Changing the p-methyl of the mesityl to electron donating and withdrawing groups may allow the adjustment of the electronic parameters without disrupting the steric bulk.

Figure 7A:
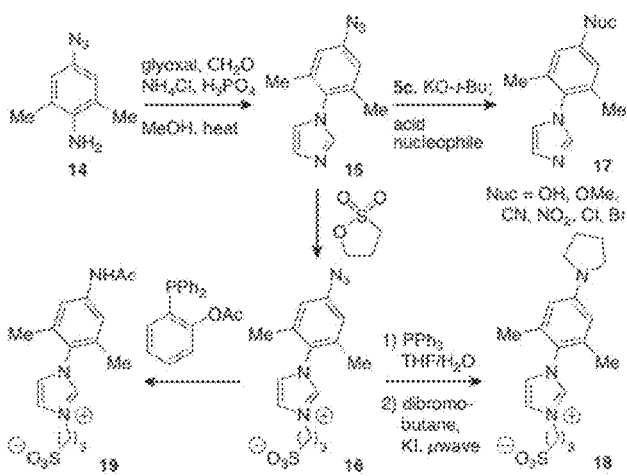
FIG. 7A, FIG. 7B, FIG. 7C, and FIG. 7D show non-limiting examples of reaction schemes involving triazabutadienes.

Referring to FIG. 7A, in some embodiments, synthesis may be performed with known p-azido dimethyl aniline (Compound 14) because it may lead to a wide range of substituted compounds. From imidazole (Compound 15) one can alkylate with 1,3-propanesultone to provide NHC precursor Compound 16, or prior to that one can treat with an NHC to access the wealth of diazonium chemistry to provide Compound 17 in all of its forms. Solvolysis in water or alcoholic solvent may provide a phenol or aryl ether, and copper mediated Sandmeyer-type chemistry may afford cyano, nitro or halogenated aryl species. From imidazolium Compound 16 Staudinger chemistry followed by aniline alkylation may provide Compound 18, or traceless Staudinger-Bertozzi ligation may yield Compound 19. These substrates cover a range of Hammett values while also providing an additional site of attachment to proteins, fluorophores, surfaces, etc.

Figure 7B:
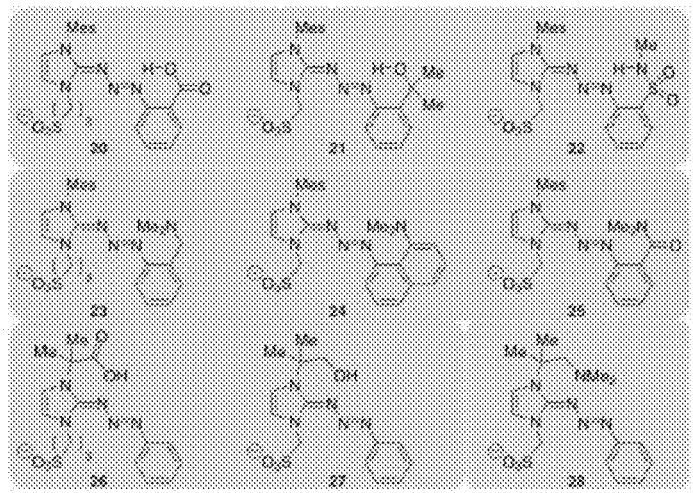
Figure 7C:
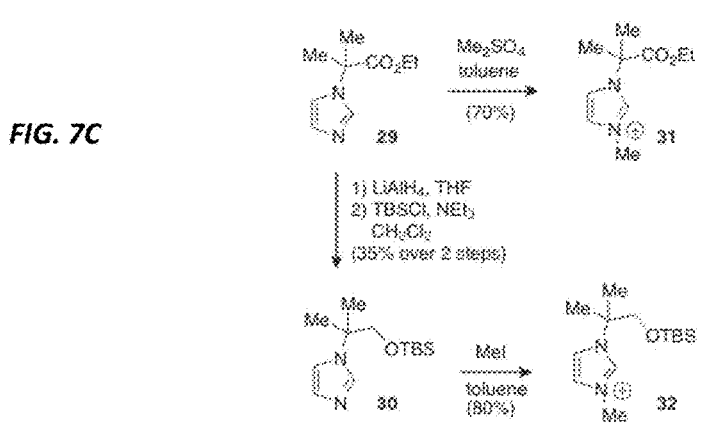

Referring to FIG. 7B, regarding the role of intramolecular hydrogen bond acceptors/donors in reactivity, it may be possible to synthesize a series of triazabutadienes with hydrogen bond donors that possess a range of pKa values (Compounds 20-22). In addition to H-bond donors, it may be possible to synthesize a series of internal bases (Compounds 23-25). It may be possible that that bases positioned near the N1 nitrogen will favor protonation at N3 and thus make the triazabutadiene less stable to acidic media. These compounds are all synthetic targets given a strategy of coupling with aryl azides. The delicate triazabutadiene functional group is installed last under mild conditions. In addition to compounds that are designed to activate/deactivate the N1 nitrogen, it may be possible to synthesize a series of compounds where the N3 nitrogen in most likely to be affected (Compounds 26-28). An NHC with a hydrogen bond donor on a short arm was made. As in FIG. 7C, the synthesis of Compounds 26-28 from known Compound 29 may start with either alkylation to a compound like Compound 31 or reduction and protection to Compound 30 followed by alkylation to Compound 32. If the mesityl is absolutely essential for a desired reactivity profile, a H-bond donor/acceptor may be inserted on a methyl group in the ortho position of the mesityl ring.

Figure 7D:
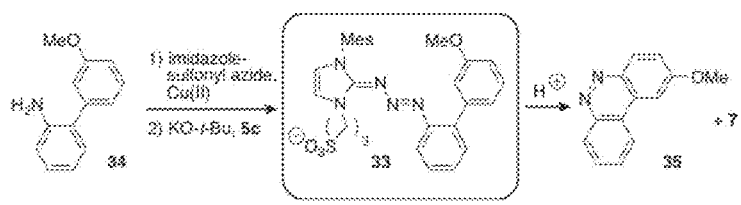

Referring to FIG. 7D, regarding intramolecular trapping of diazonium species, it may be possible to synthesize triazabutadienes with adjacent functional groups that will rapidly consume the diazonium species. For example, Compound 33 contains an aryl ring, positioned ortho to the masked diazonium. The synthesis may start from a diazo transfer reaction to convert aniline Compound 34 to an aryl azide. Coupling with Compound 5c (see FIG. 6E) may complete the synthesis. It is possible that following diazonium unmasking an aromatic substitution reaction will occur to provide benzocinnoline Compound 35. Because this reaction is intramolecular one might be able to use a non-activated ring, rendering the ring electron rich. The methyl ether may serve as a site of attachment to chemical cargos. A second type of intramolecular diazonium trap that could be employed is a beta keto ester that is also ortho to the diazonium produced. Beta keto esters are known to react with diazonium species through enol form, and can generate oxo-cinnolines, which are biologically active cores.

IV. Releasable Triazabutadienes (Pro-Triazabutadienes)
  a. Pro-Triazabutadiene Synthesis and Mechanisms The present invention also features triazabutadienes that may be released from pro-triazabutadienes (triazabutadiene precursors), e.g., under appropriate conditions. The present invention also features triazabutadienes that are used to synthesize said pro-triazabutadienes.

Inventors have surprisingly discovered that carboxylation on N1 of triazabutadienes reversibly yields stabilized or protected versions of triazabutadienes, e.g., pro-triazabutadienes that are generally stable in acidic conditions. For example, carboxylation on N1 yielded a pro-triazabutadiene molecule that is stable in concentrated HCl in methanol; treating the pro-triazabutadiene molecule with NaOH in methanol returned the original triazabutadiene molecule (which can then be degraded, e.g., in acidic conditions). Thus, the pro-triazabutadiene molecule may function as a means to protect triazabutadienes from degradation, e.g., under acidic conditions.

The present invention features pro-triazabutadiene molecules that under appropriate conditions (e.g., chemical conditions, enzymatic conditions, light, etc.) yield or release a triazabutadiene molecule. As used herein, the terms "releasable triazabutadiene" and "pro-triazabutadiene" refer to molecules that comprise an inactive form of a triazabutadiene molecule (e.g., a protected version of a triazabutadiene) but can yield or release an active triazabutadiene molecule upon appropriate conditions. The active triazabutadiene molecule could then go on to release a diazonium species. That diazonium species could then react with a phenol (e.g., a tyrosine molecule), e.g., in a coupling reaction, or the diazonium species could self-immolate to release a phenol.

The conversion of a triazabutadiene molecule to a protected triazabutadiene (or pro-triazabutadiene), e.g., carboxylation on N1, is reversible. Without wishing to limit the present invention to any theory or mechanism, it is believed that a mechanism that involves pushing electrons onto the carbonyl carbon would result in cleavage of the carbon-N1 nitrogen bond. And, there are triggered release processes that could undergo such an event. For example, some reactions are optimized to lose carbon dioxide via carbarmic acids. It is possible that a quinone methide base linker may function well for triggered release as well.

Figure 8A:
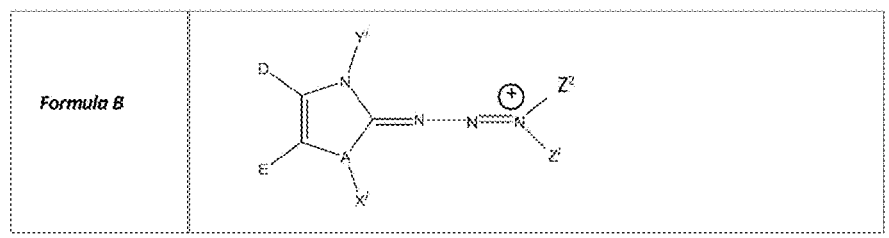
FIG. 8A shows formulas for releasable triazabutadienes of the present invention.

FIG. 8A shows a non-limiting example of a formula (Formula B) for releasable triazabutadiene molecules (pro-triazabutadiene molecules) of the present invention. In some embodiments, pro-triazabutadienes may comprise a formula according to Formula B. In some embodiments, $Z^2$ comprises a carboxyl group (N1 nitrogen is carboxylated). $X^1$ and $Y^1$ have been previously described. For example, in some embodiments, $X^1$ comprises a mesityl group. In some embodiments, $Y^1$ comprises a mesityl group. In some embodiments, $Z^2$ (the carboxyl group) comprises $CO_2Et$. The present invention is not limited to the aforementioned examples and formulas. For example, $Z^2$ may comprise a carboxyl group different from Co2Et.

In some embodiments, the pro-triazabutadienes comprise a triazabutadiene, e.g., according to Formula B, wherein the N1 nitrogen of the triazabutadiene is modified such that the modified triazabutadiene is more stabile at a particular pH as compared to the unmodified triazabutadiene. For example, in some embodiments, the modified triazabutadiene (pro-triazabutadiene) is more stabile at pH 5.5 as compared to the unmodified triazabutadiene. In some embodiments, the modification comprises carboxylation (on the N1 nitrogen). The present invention is not limited to modifications comprising carboxylation on the N1 nitrogen. In some embodiments, the modification comprises an ortho-quinone methide linked on the N1 nitrogen.

Further, the present invention is not limited to the N1 carboxylations described herein. For example, other carbonyl variations or derivatives may be used, e.g., the ethyl formate side group shown in Compound 58 of FIG. 8B may be different, e.g., the carbonyl oxygen may be replaced with sulfur, one or both oxygen atoms may be replaced with nitrogen, an oxygen atom may be removed, etc.

In some embodiments, the triazabutadiene molecules that form the pro-triazabutadiene molecules are water-soluble. In some embodiments, the triazabutadiene molecules that form the pro-triazabutadiene molecules are not water-soluble.

Figure 8B:
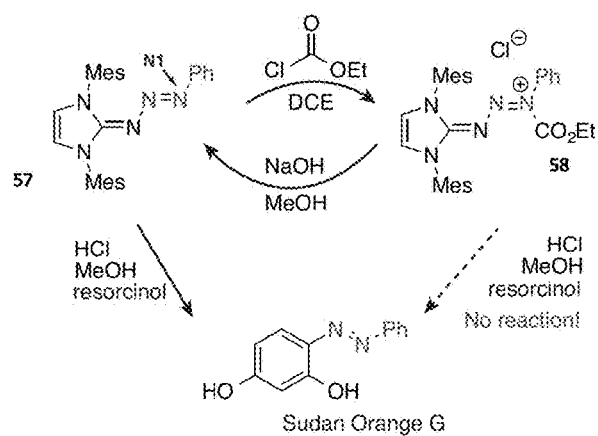
FIG. 8B shows synthesis of a pro-triazabutadiene (Compound 57) from a triazabutadiene (Compound 58) and ethylchloroformate.

To test reversibility of carboxylation on N1, triazabutadiene Compound 57 was synthesized from Compound 58 and ethylchloroformate (see FIG. 8B). It was observed that Compound 57 was stable to a 20% solution of concentrated HCl in methanol overnight (confirmed by NMR and in the presence of resorcinol). Conversely, Compound 57 readily reacted with NaOH in methanol, returning the base-stable precursor Compound 58. True to mechanism, acidification of this solution with HCl rapidly yielded the benzene diazonium ion and subsequently reacted with the resorcinol present to provide the azobenzene product, Sudan Orange G. The triazabutadiene is a nucleophile and thus stable to biological nucleophiles, such as thiols, but it is possible that thiols will now react with electrophilic Compound 57 to provide side reactions (e.g., undesirable side reactions). When Compound 57 was tested with two-fold excess of β-mercaptoethanol (BME) in methanol, it was determined that the half-life was ~20 hours. The reaction appeared to cleanly provide a neutral compound that has been reduced.

b. Triazabutadiene Release

A variety of triggers may be employed to release the triazabutadiene from the pro-triazabutadiene. The release of the triazabutadiene molecule may in some cases be selectively triggered. For example, in some embodiments, the trigger is an enzymatic trigger that selectively reacts with the protected triazabutadiene to deprotect the protected triazabutadiene, possibly allowing for aryl diazonium release.

Figure 14A:
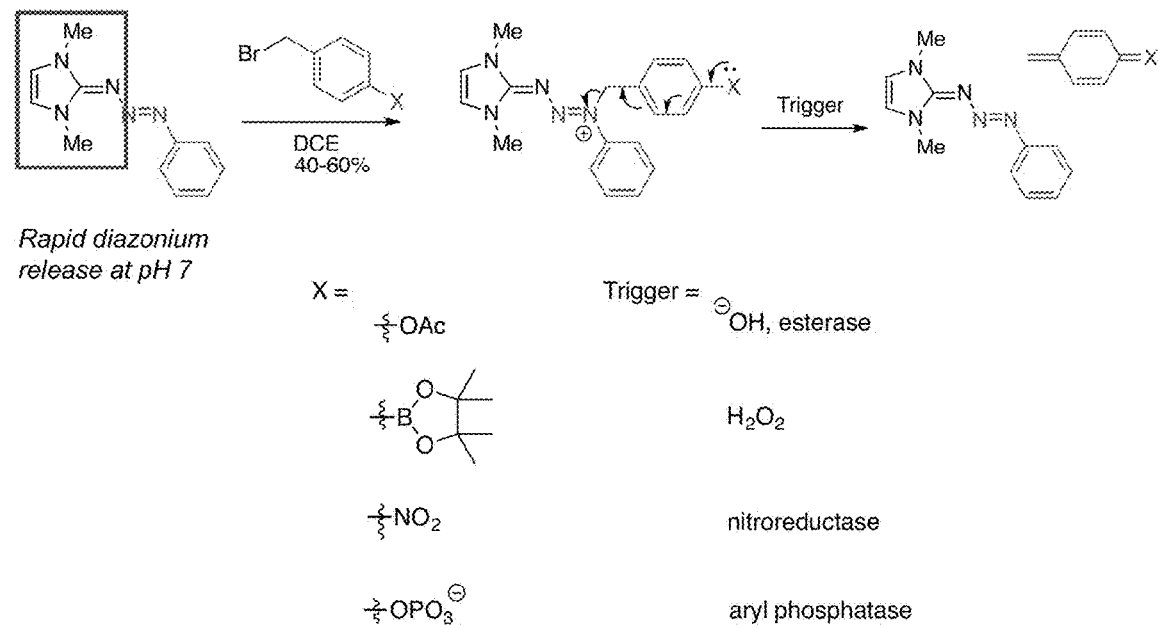
FIG. 14A shows an example of triazabutadiene (left molecule) and a reaction to create a protected the triazabutadiene (middle molecule), e.g., a triazabutadiene with N1 nitrogen protection to help prevent the rapid release of the aryl diazonium that may typically occur if the triazabutadiene is not protected. The protected triazabutadiene may, upon an enzymatic trigger (right molecule), yield an aryl diazonium species.
Figure 14B:
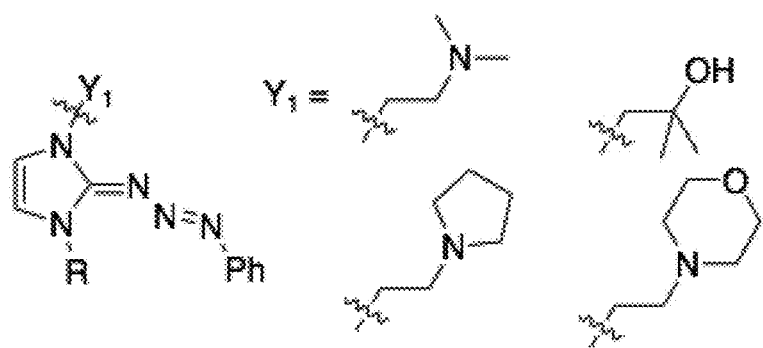
FIG. 14B shows Formula B (left) and non-limiting examples of Y$^1$.

FIG. 14A protection of a triazabutadiene to allow its selective activation via an enzymatic trigger. A triazabutadiene is shown on the left. The triazabutadiene may be converted to a protected triazabutadiene (middle molecule), e.g., pro-triazabutadiene. The protected triazabutadiene may feature protection at the N1 nitrogen to help prevent the rapid release of the aryl diazonium that may typically occur if the triazabutadiene is not protected. The protected triazabutadiene may, upon an enzymatic trigger (right molecule), yield an aryl diazonium species.

Enzymatic triggers may include but are not limited to phosphatases, sulfatases, esterases, nitroreductases, etc., or any enzyme that cleaves a bond. Such enzymes are well known to one of ordinary skill in the art. A triazabutadiene may be created or tailored to be cleavable by a particular enzyme of choice.

In some embodiments, the compound used to protect the triazabutadiene (e.g., see first reaction of FIG. 14A) may be termed a protecting group. In some embodiments, the protecting group comprises a drug or pro-drug. In some embodiments, upon an enzymatic trigger, the drug or pro-drug is released. The protecting groups are not limited to drugs; any appropriate molecule may be considered.

Figure 8C:
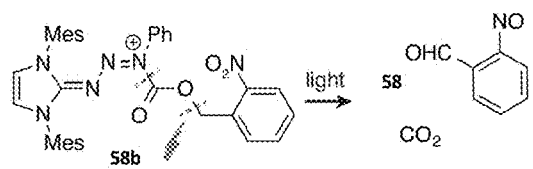
FIG. 8C shows a triggered release of a pro-triazabutadiene (Compound 58b).
Figure 8D:
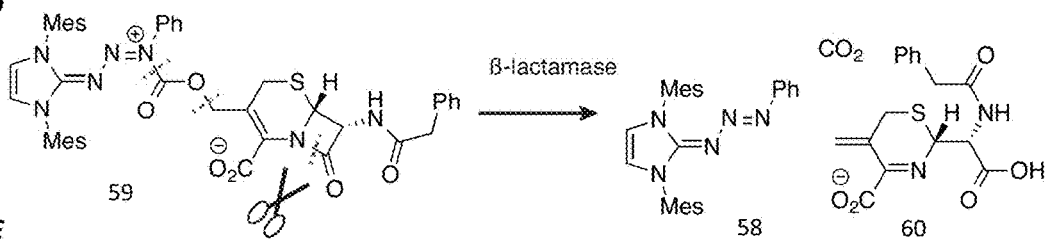
FIG. 8D shows a proposed substrate (a pro-triazabutadiene, Compound 59) for beta-lactamase. Upon cleavage of the beta-lactam, the compound will decompose to release carbon dioxide and return the triazabutadiene (Compound 58).
Figure 8E:
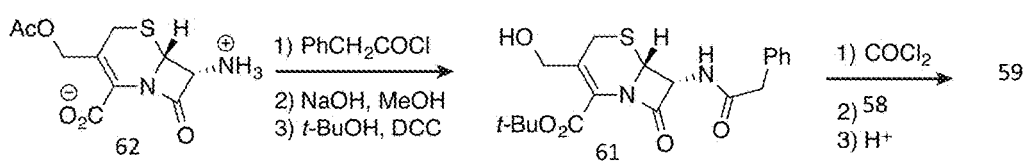
FIG. 8E shows synthesis of the pro-triazabutadiene (Compound 59) via known beta-lactam (Compound 61).

The present invention features a range of moieties that can be utilized to trigger triazabutadiene release (FIG. 8C shows one example). For example, ortho-nitro derivatives (e.g., Compound 58b) may provide photo-caged moieties. The light used to un-cage (~365 nm) may also speed up diazonium release. In addition to the photo-uncaged triazabutadienes, the present invention also features enzymatically-triggered derivatives. As an example, FIG. 8D shows β-lactamase substrate Compound 59. The strained β-lactam ring is opened whereupon the nitrogen is now in conjugation with a π-system that can facilitate the release of a leaving group and yield Compound 60. The synthesis of this compound may follow known routes to Compound 61 (from commercially available Compound 62, see FIG. 8E) to the chloroformate precursor. These enzymes are stable and catalytically active throughout the pH 5.5-8 range (which may be ideal for testing the stability of the activated triazabutadiene).

Figure 8F:
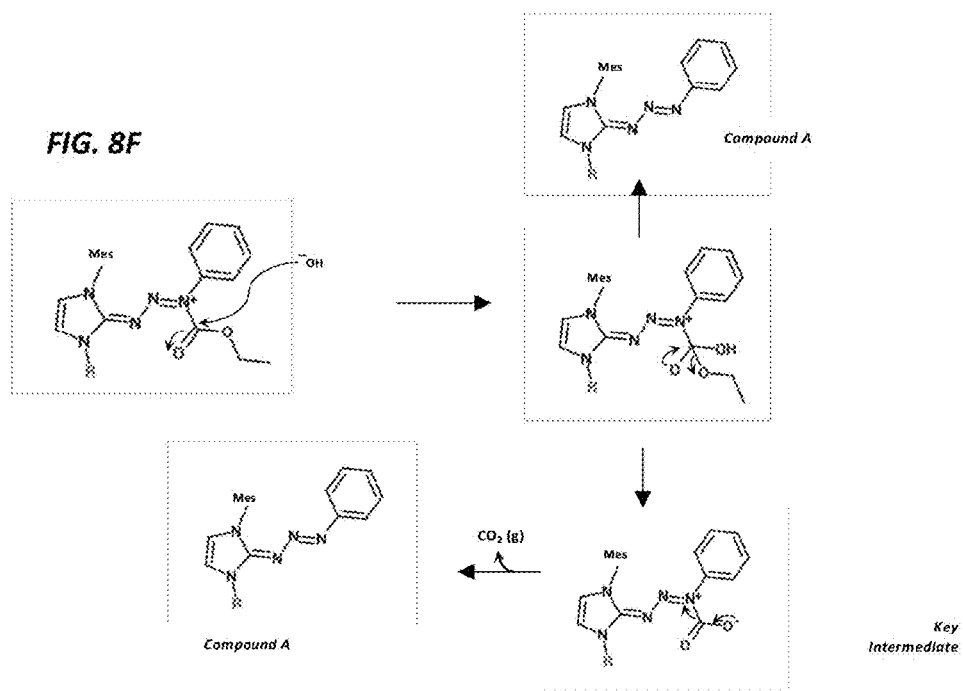
FIG. 8F shows a tetrahedral intermediate.

FIG. 8F shows a tetrahedral intermediate (see Key Intermediate). This tetrahedral intermediate may be important for release strategies. For example, the loss of carbon dioxide from the intermediate yields the original triazabutadiene (e.g., see Compound A in FIG. 8F).

Figure 8G:
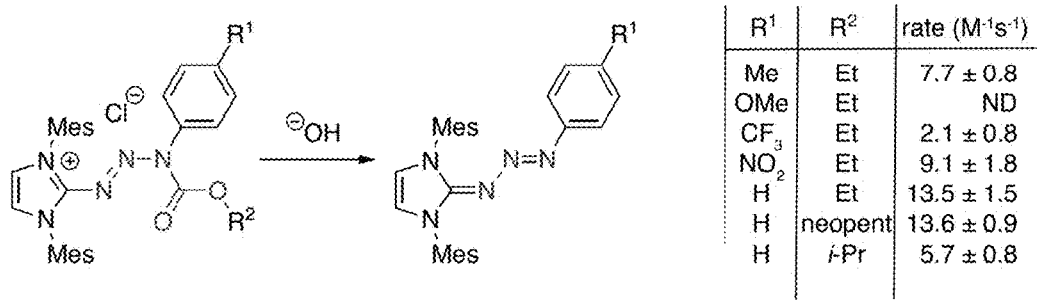
FIG. 8G shows synthesis of several protected triazabutadienes that have varying electronic properties on the aryl ring.

FIG. 8G shows synthesis of several protected triazabutadienes with varying electronic properties on the aryl ring. The inductively electron donating p-methyl substituent, 8, slowed the rate of deprotection moderately. Without wishing to limit the present invention to any theory or mechanism, it is believed that this can be rationalized by a model whereby the carbonyl is stabilized by being more electron rich and thus less prone to nucleophilic attack. The p-methoxy substituted compound, 9, also slowed hydrolysis, so much so that the rate could not be determined due to the error of the analysis. Interestingly, both the inductively electron withdrawing p-trifluoromethyl compound, 10 and resonance withdrawing p-nitro substituted 11 slowed hydrolysis, with the inductive effect playing a much larger role. Only a small change in rate was observed moving from ethyl 7 to neopentyl 12 and i-propyl 13 (for the alkyl group appended to the carbamate).

Figure 8H:
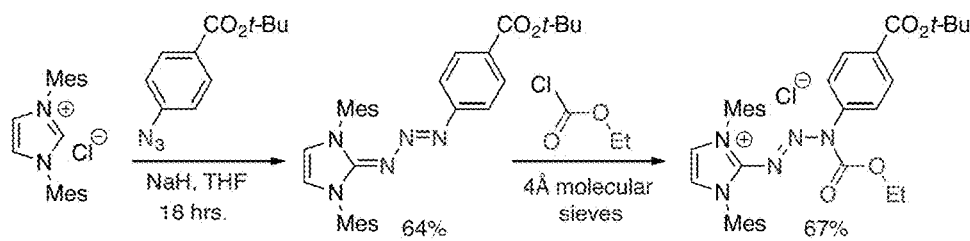
FIG. 8H shows synthesis of a protected triazabutadiene bearing a t-butyl ester.
Figure 8I:
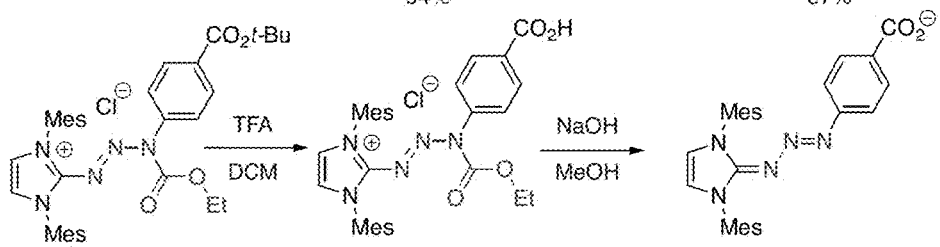
FIG. 8I shows removal of the protection of the t-butyl ester triazabutadiene of FIG. 8H under basic conditions.

In addition to rendering the triazabutadiene moiety more compatible with protein bioconjugation strategies to modify proteins of interest, the acid-stabilization may make the triazabutadiene compatible with most traditional Boc-strategies of solid-phase peptide synthesis. A protected triazabutadiene bearing a t-butyl ester was synthesized (see FIG. 8H, FIG. 8I). The acid-labile ester was removed using trifluoroacetic acid (TFA) in dichloromethane. Following removal of the ester the carbamate protection was removed under basic conditions and finally the resulting triazabutadiene was treated with acid and resorcinol to provide an azo-benzene product.

FIG. 9 shows analyses of various protected triazabutadienes. For example, FIG. 9A shows synthesis of protected triazabutadienes and their prospective yields using various chloroformate reagents. FIG. 9B shows a hydrolysis reaction of protected triazabutadienes where R=—CH$_2$CH$_3$ in buffer. The reaction is assumed to be second order with the addition of hydroxide to be the rate-determining step. FIG. 9C shows a decrease in absorbance of the protected triazabutadiene where R=—CH$_2$CH$_3$ as the hydrolysis reaction proceeds over time. Compound was in a concentration of 31 µM in 25 mM sodium borate buffer of pH 10 with scans every 60 seconds. FIG. 9D shows the concentration (µM) of protected triazabutadiene where R=—CH$_2$CH$_3$ vs. time (min). Scans were obtained every 60 seconds. (Note the initial concentration of compound was 31 µM in buffers of various pH ranges. Buffers pH 8, 9, and 10:25 mM sodium borate; buffer pH 7:100 mM phosphate; buffer pH 2:200 mM KCl buffer.) FIG. 9E shows a graph of ln(abs) vs. time (s) to obtain K$_{obs}$ under pseudo-first order reaction conditions: a plot of K$_{obs}$ vs. hydroxide concentration (M) to obtain the second order rate constant (k$_2$). The chart shows various protected triazabutadienes with their corresponding second order rate constants (k$_3$).

Figure 9A:
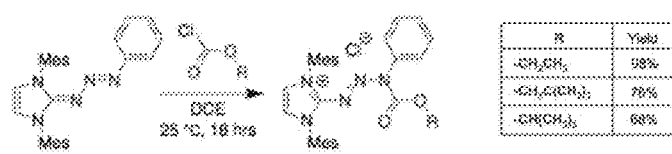
FIG. 9A shows synthesis of protected triazabutadienes and their prospective yields using various chloroformate reagents.
Figure 9B:
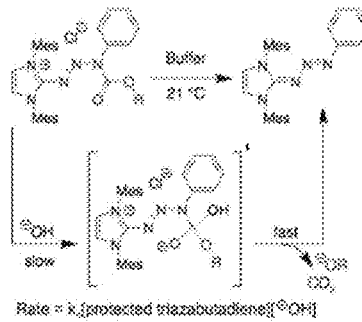
FIG. 9B shows a hydrolysis reaction of protected triazabutadienes where R=—$CH_2CH_3$ in buffer. The reaction is assumed to be second order with the addition of hydroxide to be the rate-determining step.
Figure 9C:
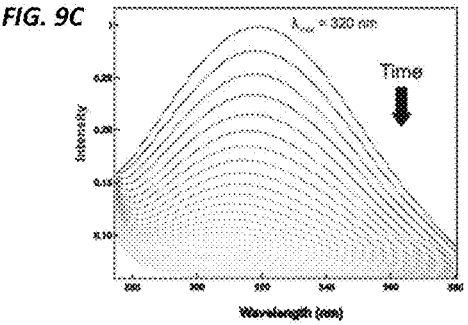
FIG. 9C shows a decrease in absorbance of the protected triazabutadiene where R=—CH$_2$CH$_3$ as the hydrolysis reaction proceeds over time. Compound was in a concentration of 31 µM in 25 mM sodium borate buffer of pH 10 with scans every 60 seconds.
Figure 9D:
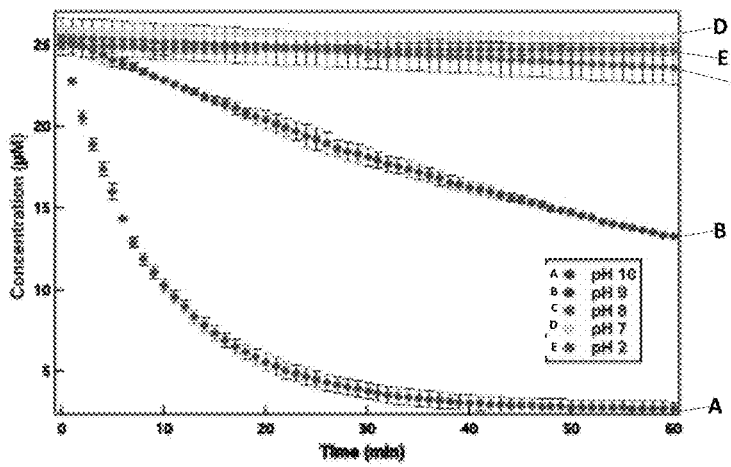
FIG. 9D shows the concentration (µM) of protected triazabutadiene where R=—CH$_2$CH$_3$ vs. time (min). Scans were obtained every 60 seconds. Initial concentration of compound was 31 µM in buffers of various pH ranges. Buffers pH 8, 9, and 10:25 mM sodium borate; buffer pH 7:100 mM phosphate; buffer pH 2:200 mM KCl buffer.
Figure 9E:
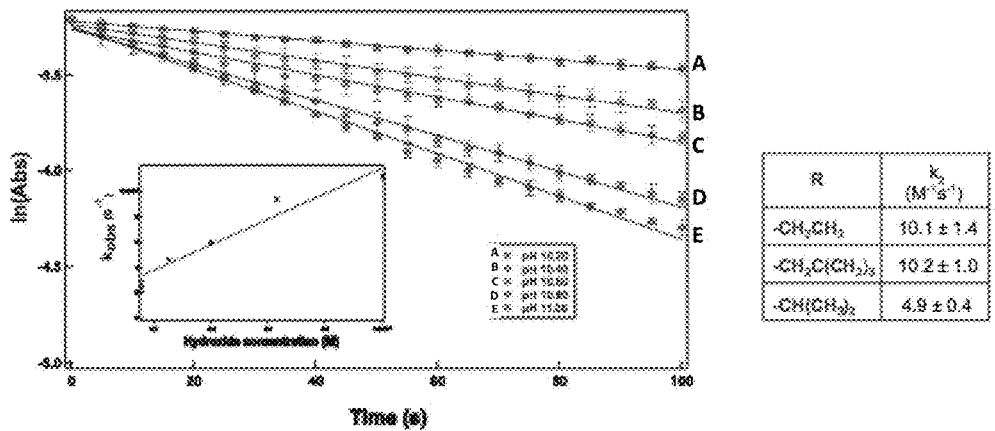
FIG. 9E shows a graph of ln(abs) vs. time (s) to obtain K$_{obs}$ under pseudo-first order reaction conditions: a plot of K$_{obs}$ vs. hydroxide concentration (M) to obtain the second order rate constant (k$_2$). The chart shows various protected triazabutadienes with their corresponding second order rate constants (k$_3$).
Figure 9F:
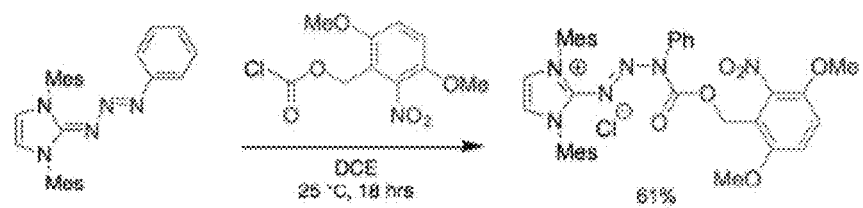
FIG. 9F shows synthesis of a protected triazabutadiene with a photocleavable protecting group.
Figure 9G:
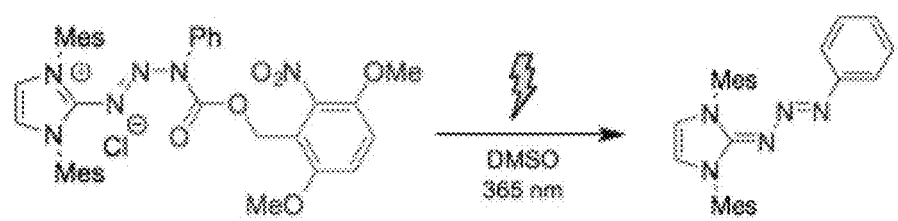
FIG. 9G shows a photocleavable protected triazabutadiene exposed to 365 nm light to yield a regular triazabutadiene.
Figure 9H:
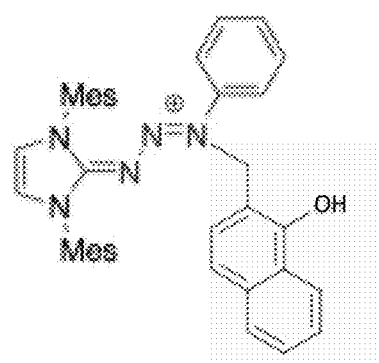
FIG. 9H shows a non-limiting example of a triazabutadiene that is photocleavable but not cleavable using acids or bases.

In some embodiments, the protected triazabutadiene is protected with a photocleavable protecting group. For example, FIG. 9F shows synthesis of a protected triazabutadiene with a photocleavable protecting group. FIG. 9G shows a photocleavable protected triazabutadiene exposed to 365 nm light to yield a regular triazabutadiene. In some embodiments, the protected triazabutadiene is not susceptible to cleavage using acids or bases. In some embodiments, the protected triazabutadiene is photocleavable (see FIG. 9H as an example of a photocleavable protected triazabutadiene that is not susceptible to cleavage using acids or bases).

The present invention also features releasable triazabutadienes that can be appended to proteins, e.g., an azide-containing compound.

The releasable triazabutadiene molecules may provide opportunities for selective diazonium delivery as biochemical probes. The releasable triazabutadiene molecules may provide for spatially selective release of aryl diazonium ions. The reactivity may be generalized to be broadly applicable and triggered. For example, by parlaying the release chemistry into amide bonds it may be possible to target proteases. And, endosomal proteases that viruses and other pathogens encounter upon entry should facilitate cleavage. If the caged triazabutadiene compounds are not substrates for the enzyme then a quinone-methide strategy may be implemented.

c. Applications for Protected/Pro-triazabutadiene Molecules

As previously discussed, a variety of triggers (e.g., enzymatic cleavage, light, base, etc.) may be employed to release the triazabutadiene from the pro-triazabutadiene. The release of the triazabutadiene molecule may in some cases be selectively triggered. Thus, the pro-triazabutadiene molecules may allow for use in two-step drug release systems or other cargo release systems. Or, the pro-triazabutadiene molecules may provide for an easier means of protein modification, e.g., because the molecules can be worked with in a wider range of pHs.

Without wishing to limit the present invention to any theory or mechanism, it is believed that the increased stability of the pro-triazabutadiene molecules in acidic environments may provide for enhanced processes of self-assembling monolayers for the production of biosensors. For example, the pro-triazabutadiene may be protected until it is in the presence of any given enzyme, and upon that trigger, the triazabutadiene molecule can be released, which can then go on to form a diazonium species, which can couple with particles such as nanoparticles, polymers, and biomacromolecules. For example, in some embodiments, the molecules of the present invention can be used to help couple target compounds to a sensor (e.g., see U.S. Pat. No. 8,668,978, the disclosure of which is incorporated herein in its entirety).

V. Applications and Methods of Use of Triazabutadienes

The triazabutadiene molecules of the present invention may be utilized for a variety of purposes. For example, in some embodiments, the triazabutadiene molecules of the present invention are utilized for a chemoselectively-cleavable linkage for use in biological/complex settings where rapid, dean cleavage is of interest. In some embodiments, the triazabutadiene molecules are used for systems including but not limited to drug delivery systems, protein-protein interaction systems, pH environment detection systems, etc. Applications of these triazabutadienes may fall under one (or more) categories of reactivity.

Diazonium Coupling Applications

Regarding diazonium coupling, the triazabutadiene molecules may be used for applications involving pH-dependent protein coupling. General examples involve methods for detecting protein-protein proximity or protein-protein interactions (in a sample). In some embodiments, the method comprises providing a first protein, wherein the first protein is conjugated with a triazabutadiene molecule according to the present invention. The first protein may be introduced to a sample. In some embodiments, the triazabutadiene molecule encounters a low pH in the sample; in some embodiments, acid is added to the sample to lower the pH appropriately. As previously discussed, in the low pH environment, the triazabutadiene molecule undergoes the irreversible reaction yielding the diazonium species and the cyclic guanidine species. As previously discussed, the diazonium species is adapted to react with a phenol group; thus if there is a nearby protein with a tyrosine residue, the diazonium species may react with it yielding an azobenzene product (often colored, e.g., the dye Sudan Orange G is an azobenzene-containing dye) that is visually distinct from the triazabutadiene molecule and the diazonium species. As such, detection of the azo dye (e.g., Sudan Orange) may be indicative of proximity or interaction of the first protein and the second protein. Thus, in some embodiments, the method comprises adding a second protein to the sample, wherein a tyrosine of the second protein may react with the diazonium species. In some embodiments, the second protein is already in the sample. In some embodiments, a tyrosine or phenol species conjugated to the second protein.

In some embodiments, the method comprises introducing to the sample a first antibody specific for a first protein, wherein the first antibody is conjugated with a triazabutadiene molecule according to the present invention. In some embodiments, the method comprises introducing to the sample a second antibody specific for a second protein. In some embodiments, the second antibody comprises a tyrosine. In some embodiments, the second antibody is conjugated with a phenol species. In some embodiments, the method comprises introducing an acid to the sample to appropriately lower the pH of the sample. As previously discussed, in the low pH environment, the triazabutadiene molecule undergoes the irreversible reaction yielding the diazonium species and the cyclic guanidine species. As previously discussed, the diazonium species is adapted to react with a phenol group; thus if the phenol species is nearby, the diazonium species may react with it yielding an azo dye that is visually distinct from the triazabutadiene molecule and the diazonium species. As such, detection of the azo dye may be indicative of proximity or interaction of the first protein and the second protein.

Figure 10A:
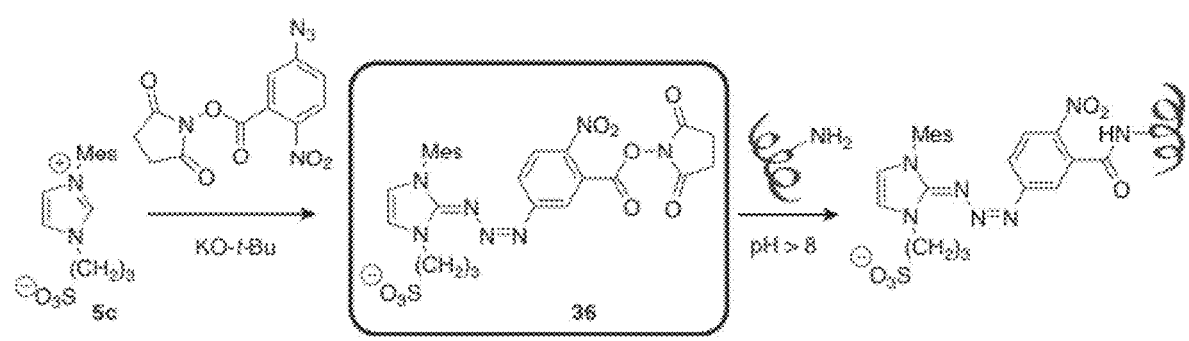
FIG. 10A shows an example of a triazabutadiene molecule adapted to modify a protein.

As a more specific example, the acid-labile reactivity of triazabutadienes may be used to assist in work deducing interaction partners between a virus and endosomally localized host proteins. Upon endosomal acidification a viral-bound diazonium species may be unmasked and this may go on to react with Tyr-containing proteins that are associating with the virus. It is possible that this system could be used to trap an interaction that is relevant at a key point of viral entry, e.g., the fusion of membranes. Herein are non-limiting examples of synthesis of compounds that may be used in such systems, e.g., for modifying the viral surface. Lysine-reactive probes may be used to modify the surface of viral proteins. Referring to FIG. 10A, by synthesizing triazabutadiene Compound 36 bearing an N-hydroxysuccinimide (NHS) ester it may be possible to couple the compound to one of many reactive Lys on the surface of the virus. As previously discussed, a triazabutadiene molecule may be attached to a viral protein (e.g., a purified viral protein). Then, a system such as a cell line (e.g., mosquito cell line, human cell line, or even mosquitoes themselves) may be infected with the viral protein. The infected system can be treated appropriately. The azo dye may "label" any proteins that interact with or are nearby the viral protein (in the low pH environment). The present invention is not limited to this example.

Figure 10B:
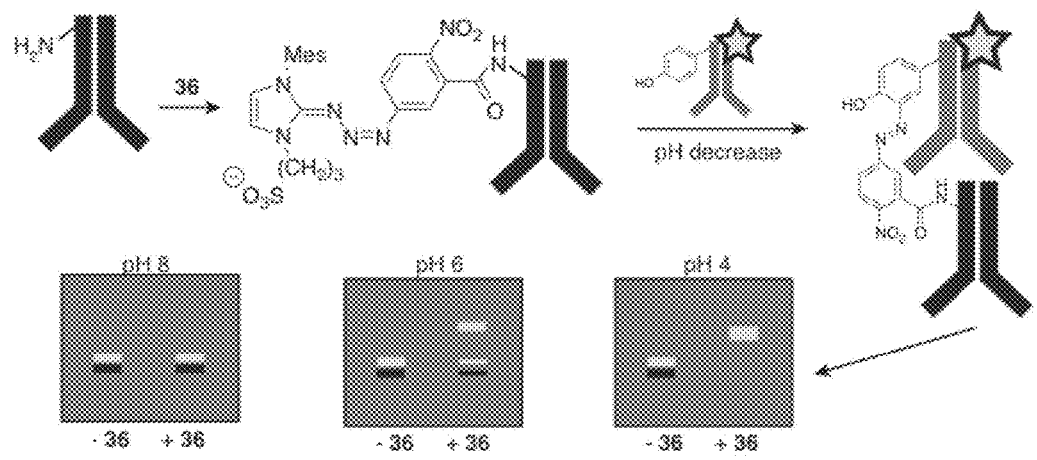
FIG. 10B shows an example of a triazabutadiene molecule conjugated to an antibody, wherein the conjugate is used for labeling a protein of interest.

Lys-NHS conjugation chemistry may work well on the basic side of neutral, which may be beneficial for pH sensitive probes. Referring to FIG. 10A and FIG. 10B, Compound 36 may be made in a straightforward fashion from NHC precursor Compound 5c (see FIG. 6E) and an aryl azide. It is possible that the steric congestion about the NHC may favor the unencumbered azide over the potentially reactive NHS ester. If the NHS ester presents a problem during the synthesis it is possible to go into the reaction with a carboxylate instead and follow that by a coupling with N-hydroxysuccinimide. If electronically coupling the NHS ester to the aryl system is detrimental to reactivity it is possible to consider inserting an alkyl or, if needed for additional solubility, polyethylene glycol (PEG) linker. As an example, referring to FIG. 10B, a monoclonal antibody (e.g., mouse anti-biotin) may be modified with Compound 36. Once the surface is decorated with triazabutadienes, the extent of labeling may be quantified by coupling to resorcinol (or other appropriate alternative) in a low pH solution and the extent of modification may be analyzed by mass spectrometry. This may show the number of reactive triazabutadienes. Following this analysis, a fluorescent goat anti-mouse secondary antibody may be added, and then a gel-shift assay may be used to show that the two antibodies are covalently linked in a pH dependent manner.

b. Triazabutadiene Probes for Protein Modification

Figure 11A:
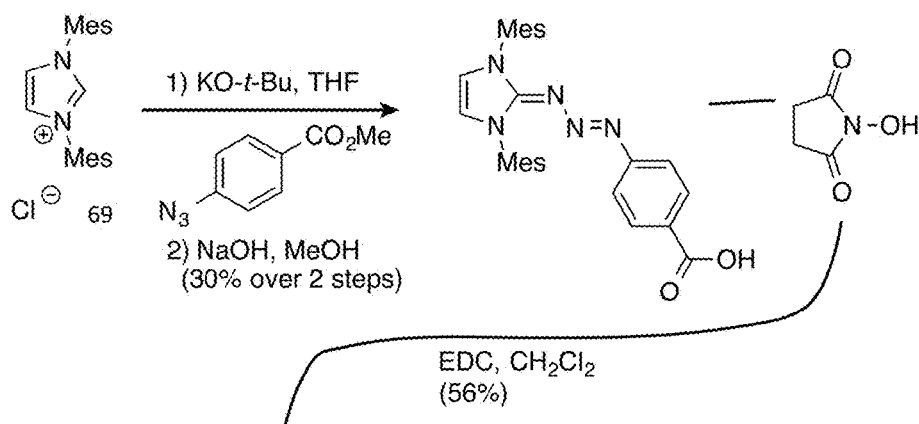
FIG. 11A shows synthesis of a triazabutadiene containing an N-hydroxysuccinimide ester.
Figure 11B:
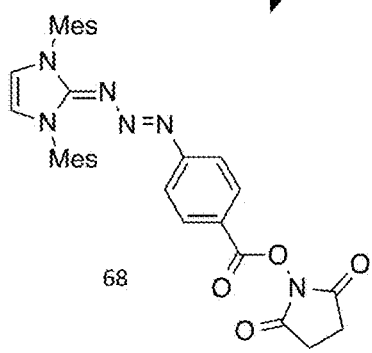
FIG. 11B shows Compound 68.
Figure 11C:
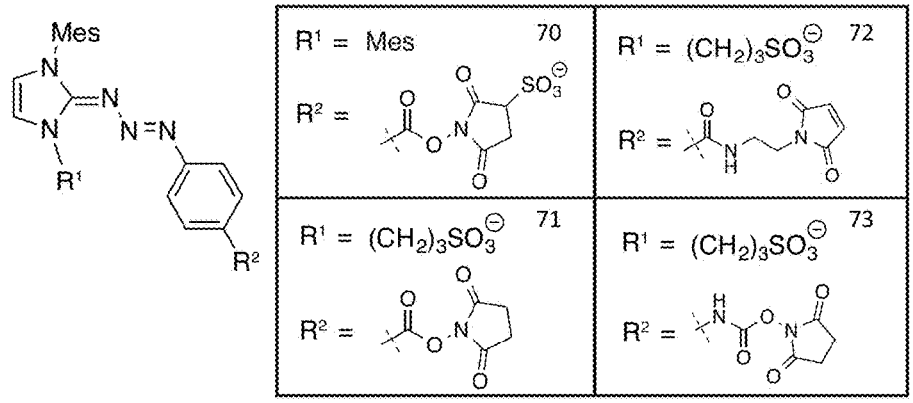
FIG. 11C shows derivatives related to Compound 68.

The present invention also features a lysine-reactive N-hydroxysuccinimide (NHS) modified triazabutadiene, e.g., Compound 68 (see FIG. 11A). This was synthesized from bismestiyl imidazolium, e.g., Compound 69 (FIG. 11B). A series of derivatives is shown in FIG. 11C. Several variants of Compound 68 may be synthesized and tested. For example, Compound 70 with a sulfonate-containing NHS ester may provide a protein modified identically to using Compound 8, but it is may be soluble at higher concentrations, which may enable more rapid labeling of dilute protein samples (such as viral samples). Another sulfonate-containing derivative, Compound 71, may have the effect of adding a negative charge to the surface of the protein that it modifies. A third probe that may be synthesized, Compound 72, contains a cysteine (thiol) reactive maleimide, which may offer a greater degree of selectivity due to the low abundance of surface exposed thiols. This probe may be used in conjunction with proteins that have been mutated to possess a solvent expose cysteine at positions of interest. The N-linked amide probe, Compound 73, may be used to look at those electronic effects in the context of a complex biological sample.

Figure 12:
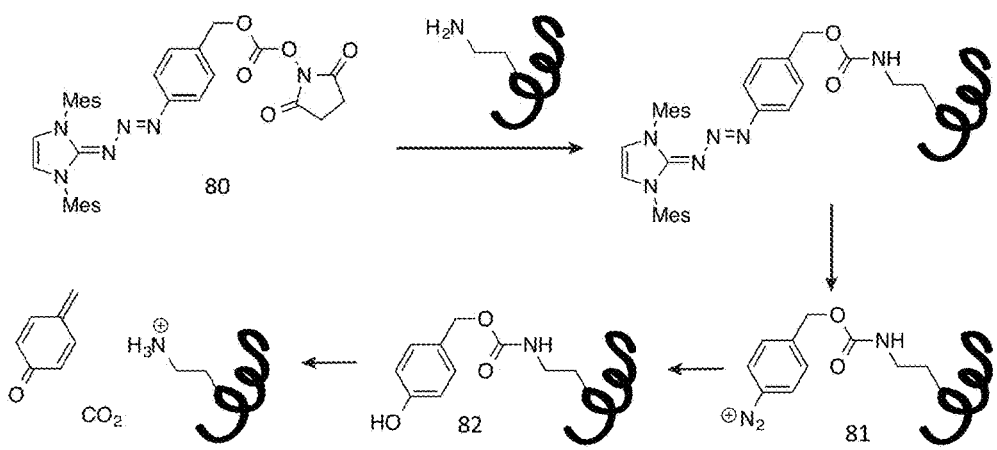
FIG. 12 shows lysine-reactive triazabutadiene Compound 80 is designed to self-immolate to return the starting lysine residue if the resulting diazonium ion, Compound 81, fails to undergo a reaction with tyrosine.

In the absence of a protein cross-linking event, there may be an aryl diazonium, which decomposes to a phenol and remains bound to the lysine. This phenol is likely prone to redox chemistry and as such represents an avenue for complexity during proteomic analysis. A self-immolating triazabutadiene has been designed to circumvent these pitfalls. Referring to FIG. 12, triazabutadiene Compound 80 provides an aryl diazonium (Compound 81), which can go on to react with locally available tyrosine residues, or decompose to phenol Compound 82 if none are available. This phenol will further degrade via quinone-methide chemistry to extrude carbon dioxide and return an unaltered lysine residue.

c. Diazonium Degradation for Cargo or Drug Release

In some embodiments, the triazabutadiene molecules of the present invention may be used in applications involving diazonium degradation to release cargo or drugs. For example, a group of applications takes advantage of the solvolysis of diazonium salts to produce phenolic byproducts. The degradation of diazonium salts to phenols, via aryl cations, is a first-order process that is not pH dependent in the physiological range of pHs. The half-life of this first order process depends on substitution on the aryl ring; the rate for benzenediazonium is ~4 hours. Indeed, the product of this degradation and subsequent azo-dye formation was observed if resorcinol is not put into the buffered NMR experiments.

In some embodiments, the acid-dependent instability of the triazabutadiene molecule may allow for a drug or cargo molecule to be deposited at a desired location and time (e.g., the reaction can be controlled and initiated at a desired time and location). As such, the present invention also features methods of delivering a drug (or a cargo compound) to a subject. In some embodiments, the method comprises providing a triazabutadiene molecule according to the present invention, conjugating a drug (or cargo compound) to the triazabutadiene molecule; and administering the conjugate (the drug/cargo-triazabutadiene conjugate) to the subject. In some embodiments, the method comprises providing a triazabutadiene molecule according to the present invention wherein the triazabutadiene molecule comprises the drug (or cargo compound); and administering the triazabutadiene molecule to the subject. In some embodiments, the diazonium species of the triazabutadiene molecule is part of the drug (or cargo compound). In some embodiments, the drug (or cargo compound) is formed when the diazonium species reacts to a phenol species. In some embodiments, the drug is an anti-cancer drug. The drug (or cargo compound) is not limited to an anti-cancer drug. Any appropriate drug for any appropriate condition may be considered. Likewise, the triazabutadiene molecules may be incorporated into drug/cargo-delivery systems for conditions including but not limited to cancer or other conditions associated with low pH states (e.g., gastrointestinal conditions, sepsis, ketoacidosis, etc.). Non-limiting examples of drugs (e.g., drugs that have a phenolic functional group, which may be masked as prodrugs) include: Abarelix, Alvimopan, Amoxicillin, Acetaminophen, Arformoterol, Cefadroxil, Cefpiramide, Cefprozil, Clomocycline, Daunorubicin, Dezocine, Epinephrine, Cetrolrelix, Etoposide, Crofelemer, Ezetimibe, Idarubicin, Ivacaftor, Hexachlorophene, Labetalol, Lanreotide, Levodopa, Caspofungin, Butorphanol, Buprenorphine, Dextrothyroxine, Doxorubicin, Dopamine, Dobutamine, Demeclocycline, Diflunisal, Dienestrol, Diethylstilbestrol, Doxycydine, Entacapone, Arbutamine, Apomorphine, Baisalazide, Capsaicin, Epirubicin, Esterified Estrogens, Estradiol Valerate, Estrone, Estradiol, Ethinyl Estradiol, Fulvestrant, Goserelin, Fluorescein, Indacaterol, Levosalbutamol, Levothyroxine, Liothyronine, Lymecycline, Mitoxantrone, Monobenzone, Morphine, Masoprocol, Mycophenolic Acid, Phenylephrine, Phentolamine, Oxytetracycline, Rifaximin, Rifapentine, Oxymetazoline, Raloxifene, Tolcapone, Terbutaline, Tetracycline, Mesalamine, Metaraminol, Methyldopa, Minocycline, Nabilone, Nalbuphine, Nelfinavir, Propofol, Rotigotine, Ritodrine, Salbutamol, Sulfasalazine, Salmeterol, Tapentadol, Tigecycline, Tolterodine, Teniposide, Telavancin, Topotecan, Triptorelin, Tubacurarine, Valrubicin, Vancomycin, etc.

In some embodiments, drug delivery systems featuring triazabutadiene molecules may be enhanced with other reactions, e.g., enzymatic reactions. Such additional reactions may help provide appropriate specificity of the drug delivery system or appropriate timing to the drug delivery system.

Figure 13A:
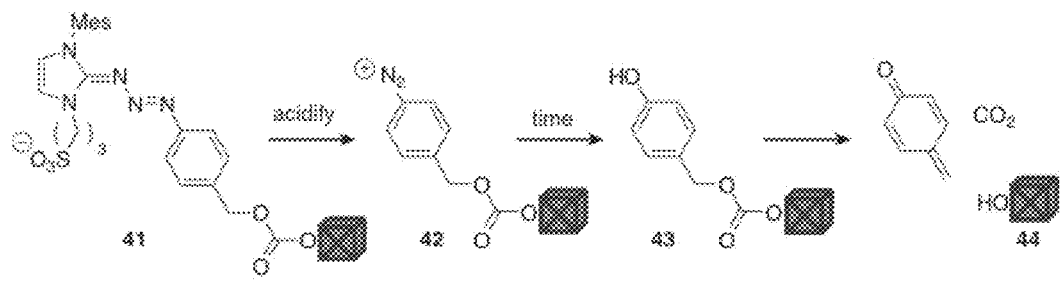
FIG. 13A shows an example of cargo release from a triazabutadiene molecule.

Referring to FIG. 13, the triazabutadiene molecules of the present invention may be used for applications involving benzoquinone methides, e.g., it may be possible to synthesize derivatives that can undergo elimination via para-quinone methide chemistry (see FIG. 13A). Referring to FIG. 13A, after acidification, triazabutadiene Compound 41 may decompose to diazonium salt (Compound 42). This reactive species may decompose to a phenol (Compound 43), which itself decomposes to a quinone methide and may liberate the cargo molecule (Compound 44). It may be possible to modify the electronic properties of the central ring in order to influence the rates at each step. This system is may be useful for these modifications because none of them are expected to affect the cargo. The azide-coupling chemistry may render this amenable to wide variety of chemical cargos. In a biological context these compounds may be able to release their desired cargo upon entry into the endosome, or upon exposure to non-virally relevant acidic environments such as in proximity to cancerous tumors. This type of attachment chemistry may be utilized as a method for drug or detection delivery, and may have an added level of specificity if the system was delivered to a desired location using an antibody or aptamer.

Figure 13B:
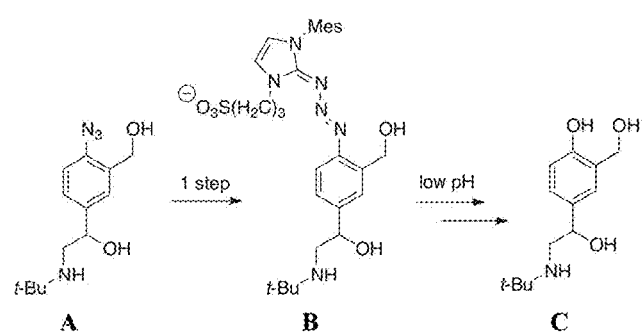
FIG. 13B shows an example of how a prodrug is released.
Figure 13C:
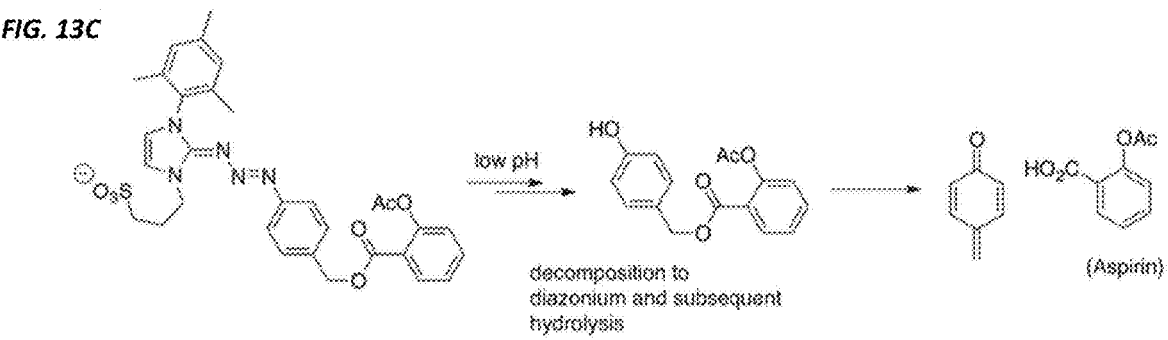
FIG. 13C shows an example of a prodrug comprising a phenolic functional group masked as a triazylidine moiety.
Figure 13D:
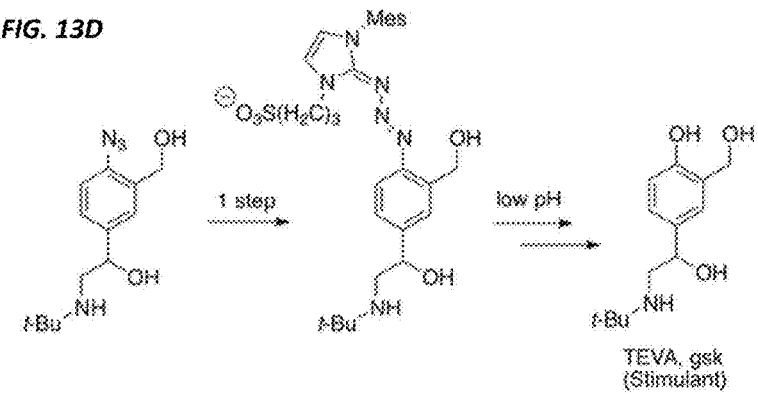
FIG. 13D shows an azide functional group reacted with a carbine to produce an acid labile prodrug comprising a triazylidine moiety.

In some embodiments, $Z^1$ (see FIG. 1, FIG. 13C) is a prodrug comprising a phenolic functional group, wherein the phenolic group is masked as a triazylidene moiety. An example of how a prodrug is released (e.g., in an acidic environment, e.g., in a patient) is illustrated in FIG. 13B. Without wishing to limit the present invention to any theory or mechanism, it is believed that all drugs, such as those approved by the U.S. Food and Drug Administration, that have a phenolic functional group may be masked as a triazylidene moiety.

Referring to FIG. 13B, Compound C is a stimulant that is produced by Glaxo Smith-Kline Beecham pharmaceutical company. The phenolic group of Compound C can be converted to an azide group, e.g., by displacement of the hydroxyl group with an azide group. In some embodiments, the phenolic group is first converted to a suitable leaving group before subjecting to a nucleophilic displacement reaction with an azide group. The resulting azide Compound A is then reacted with 3-(3-mesityl-2-(phenyltriaz-2-en-1-ylidene)-2, 3-dihydro-1H-imidazol-1-yl) propane-1-sulfonate to produce triazylidene Compound B. In some embodiments, when Compound B is administered to a patient (e.g., orally or intravenously), the acidic environment of the patient's gastrointestinal tract (if administered orally) or patient's blood plasma (when administered intravenously) decomposes it to generate a corresponding diazonium compound regenerates the phenolic group as illustrated in FIG. 13B. By converting the phenolic group (e.g., the hydroxyl group that is attached to a phenyl ring) to an azide, one skilled in the art having read the present application can readily convert the phenol compound to a triazylidene compound of the invention. Thus, the triazylidene moiety serves as a masking group for a phenolic functional group.

The present invention also features a method for administering a drug comprising a phenolic function group to a subject in need of such a drug administration. In some embodiments, the method comprises converting a drug comprising a phenolic-functional group to a prodrug, wherein said prodrug comprises an acid labile triazylidene moiety; and administering said prodrug to a subject in need of such a drug administration. In some embodiments, the triazylidene compound may also comprise a water solubility conferring moiety and/or $Y^1$ functional group defined in FIG. 1.

The present invention also features a method of converting a drug comprising a phenolic-function group to an acid labile prodrug. In some embodiments, the phenolic-functional group is converted to an azide group. The azide functional group may then be reacted with a carbene to produce an acid labile prodrug comprising a triazylidene moiety (see FIG. 13D).

d. Other Applications

In some embodiments, a triazabutadiene molecule is conjugated to another molecule (a conjugate molecule), e.g., a protein (e.g., an amino acid such as but not limited to lysine), a lipid, or other appropriate molecule. In some embodiments, the diazonium species part of the triazabutadiene molecule is conjugated to the conjugate molecule. In some embodiments, the cyclic guanidine species part of the triazabutadiene molecule is conjugated to the conjugate molecule. In some embodiments, the triazabutadiene molecule is attached to the conjugate molecule via a linker. Linkers are well known to one of ordinary skill in the art and may include (but are not limited to) a polyether linkers such as polyethylene glycol linkers. In some embodiments, the conjugate molecule to which the triazabutadiene molecule is conjugated comprises an antibody or a fragment thereof. In some embodiments, the conjugate molecule to which the triazabutadiene molecule is conjugated comprises a viral protein.

In some embodiments, the triazabutadiene molecules of the present invention are used for pull-down studies wherein a biomolecule or protein of interest is attached to one side and the other side is appended to something such as but not limited to a small molecule (e.g., hapten such as biotin) or compound. Using biotin as an example, the biomolecule or protein of interest can be pulled down using an avidin bead (which binds strongly to the biotin) and thoroughly washed. This may be useful for protein enrichment. The biomolecule or protein of interest may then be cleaved from the avidin bead by means of reductive cleavage of the triazabutadiene that holds them together. The present invention is not limited to these components, for example this application could also feature the use of a probe (e.g., fluorescent or otherwise) attached to an antibody used to interrogate a complex sample.

In some embodiments, reductive cleavage of triazabutadiene molecules may also be used to cleave unreacted triazabutadienes that did not undergo diazonium formation/reaction chemistry that is associated with a drop in pH (or other mechanism) as described above (a sort of quench for the pH chemistry).

As previously discussed, the diazonium species can react with a phenol species such as resorcinol or other appropriate phenol species. In some embodiments, a phenol species or resorcinol species is conjugated to a protein, e.g., a protein different from the protein to which the triazabutadiene molecule is conjugated, a protein that is the same protein to which the triazabutadiene molecule is conjugated, etc. In some embodiments, the resorcinol species or phenol species that the diazonium species reacts with is the phenol functional group of a tyrosine residue.

The present invention also features a method of detecting an environment having a low pH. In some embodiments, the method comprises providing a sample (e.g., tissue sample, cell sample, any appropriate sample) and introducing a triazabutadiene molecule according to the present invention to the sample. An environment having a low pH (a low pH appropriate for the triazabutadiene molecule) causes the triazabutadiene molecule to break down into a diazonium species and a cyclic guanidine species. Since the diazonium species is visually distinct from the triazabutadiene, visualization of the diazonium species is indicative of the low pH environment. In some embodiments, the method further comprises introducing a resorcinol species or a phenol species to the sample. The resorcinol species or phenol species may react with the diazonium species to form an azo dye. Since the azo dye is visually distinct from the diazonium species and the triazabutadiene species, detection of the diazonium species and/or the azo dye would be indicative of the low pH environment.

The present invention is not limited to the methods and uses described herein. For example, in some embodiments, the triazabutadiene molecules are used as reagents in buffers for various chemical or biochemical assays (e.g., immunohistochemistry assays, in situ hybridization assays, protein assays such as western blots, ELISAs, etc.).

The triazabutadiene molecules may function as masked compounds that, when exposed to water, form reaction products that form covalent bonds with surfaces containing phenols. In some embodiments, the triazabutadiene molecule (or a diazonium species) is conjugated to a molecule other than a glass or plastic as described above. In some embodiments, the triazabutadiene molecule (or a diazonium species) is conjugated to a surface via a linker. Linkers are well known to one of ordinary skill in the art and may include (but are not limited to) a polyether linkers such as polyethylene glycol linkers.

In some embodiments, a triazabutadiene molecule is bonded to a surface. Surfaces may include but are not limited to glass, plastic, a biomaterial, or any other appropriate surface, Non-limiting examples of materials also include Tufnol materials such as phenolic cotton laminated plastics, phenolic paper laminated plastics, etc., a phenol formaldehyde resin such as bakelite (or baekelite), etc.

The present invention is not limited to the methods and uses described herein. For example, in some embodiments, the molecules herein are used as reagents in buffers for various chemical or biochemical assays (e.g., immunohistochemistry assays, in situ hybridization assays, protein assays such as western blots, ELISAs, etc.).

The disclosures of the following documents are incorporated in their entirety by reference herein: U.S. Pat. No.

8,617,827; U.S. Pat. Application No. 2009/0048222; U.S. Pat. No. 3,591,575. U.S. Pat. Nos. 3,607,542; 4,107,353; WO Pat. No. 2008090554; U.S. Pat. No. 4,218,279; U.S. Pat. App. No. 2009/0286308; U.S. Pat. Nos. 4,356,050; 8,603,451; 5,856,373; 4,602,073; 3,959,210. The disclosures of the following publications are incorporated in their entirety by reference herein: Kimani and Jewett, 2015, *Angewandte Chemie International Edition* (DOI: 10.1002/anie.201411277—Online ahead of print). Zhong et al., 2014, Nature Nanotechnology 9, 858-866; Stewart et al., 2011, J Polym Sci B Polym Phys 49(11):757-771; Poulsen et al., 2014, Biofouling 30(4):513-23; Stewart, 2011, Appl Microbiol Biotechnol 89(1):27-33; Stewart et al., 2011, Adv Colloid Interface Sci 167(1-2):85-93; Hennebert et al., 2015, Interface Focus 5(1):2014.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

The invention claimed is:
1. A compound of Formula B:

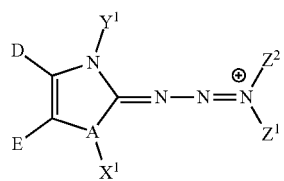

Formula B wherein:
A is —N—;
D is H;
E is H;
$X^1$ is alkyl or aryl, wherein the alkyl is optionally substituted with one or more substituents independently selected from the group consisting of C(O)OH, $NH_2$, and OH, and further wherein the aryl is optionally substituted with one or more substituents independently selected from the group consisting of alkyl, C(O)OH, $NH_2$, and OH;
$Y^1$ is alkyl or aryl, wherein the alkyl is optionally substituted with one or more substituents independently selected from the group consisting of C(O)OH, $NH_2$, and OH, and further wherein the aryl is optionally substituted with one or more substituents independently selected from the group consisting of alkyl, C(O)OH, $NH_2$, and OH;
$Z^1$ is aryl, wherein the aryl is optionally substituted with a substituent selected from the group consisting of $NO_2$, $C_{1-6}$ alkyl, $C_{1-6}$ haloalkyl, C(O)OH, C(O)O$C_{1-6}$ alkyl, and O$C_{1-6}$ alkyl; and
$Z^2$ is C(O)O$C_{1-16}$ alkyl, wherein the $C_{1-16}$ alkyl is optionally substituted with a substituent selected from the group consisting of heterocyclyl and aryl, and further wherein the heterocyclyl is optionally substituted with one or more substituents independently selected from the group consisting of oxo, $NO_2$, C(O)O$^-$, NHC(O)CH$_2$Ph, and O$C_{1-6}$ alkyl, and the aryl is optionally substituted with one or more substituents independently selected from the group consisting of $NO_2$, C(O)O$^-$, NHC(O)CH$_2$Ph, O$C_{1-6}$ alkyl, and OC(O)alkyl.

2. A compound of Formula B:

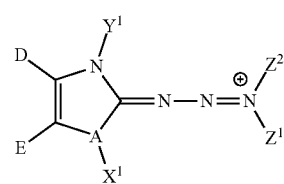

Formula B wherein:
A is —N—;
D is H;
E is H;
$X^1$ is alkyl or aryl, wherein the alkyl is optionally substituted with one or more substituents independently selected from the group consisting of C(O)OH, $NH_2$, and OH, and further wherein the aryl is optionally substituted with one or more substituents independently selected from the group consisting of alkyl, C(O)OH, $NH_2$, and OH;
$Y^1$ is alkyl or aryl, wherein the alkyl is optionally substituted with one or more substituents independently selected from the group consisting of C(O)OH, $NH_2$, and OH, and further wherein the aryl is optionally substituted with one or more substituents independently selected from the group consisting of alkyl, C(O)OH, $NH_2$, and OH;
$Z^1$ is aryl, wherein the aryl is optionally substituted with a substituent selected from the group consisting of $NO_2$, $C_{1-6}$ alkyl, $C_{1-6}$ haloalkyl, C(O)OH, C(O)O$C_{1-6}$ alkyl, and O$C_{1-6}$ alkyl; and
$Z^2$ is C(O)O$C_{1-6}$ alkyl, wherein the $C_{1-6}$ alkyl is optionally substituted with a substituent selected from the group consisting of heterocyclyl and aryl, and further wherein the heterocyclyl is optionally substituted with one or more substituents independently selected from the group consisting of oxo, $NO_2$, C(O)O$^-$, NHC(O)CH$_2$Ph, and O$C_{1-6}$ alkyl, and the aryl is optionally substituted with one or more substituents independently selected from the group consisting of $NO_2$, $C(O)O^-$, $NHC(O)CH_2Ph$, $OC_{1-6}$ alkyl, and $OC(O)$alkyl.

3. The compound of claim 2, wherein $X^1$ is $CH_3$.
4. The compound of claim 2, wherein $Y^1$ is $CH_3$.
5. The compound of claim 2, wherein $Y^1$ is $C(CH_3)_3$.
6. The compound of claim 2, wherein:
$X^1$ is alkyl; and
$Y^1$ is alkyl.
7. The compound of claim 2, wherein:
$X^1$ is $CH_3$; and
$Y^1$ is $CH_3$.
8. The compound of claim 2, wherein:
$X^1$ is $C(CH_3)_3$; and
$Y^1$ is $C(CH_3)_3$.

* * * * *